US011480519B2

(12) United States Patent
Watts et al.

(10) Patent No.: US 11,480,519 B2
(45) Date of Patent: Oct. 25, 2022

(54) METHODS, APPARATUSES, AND SYSTEMS FOR IMPROVING GAS DETECTING DEVICES

(71) Applicant: Honeywell International Inc., Morris Plains, NJ (US)

(72) Inventors: Rodney Royston Watts, Dorset (GB); Antony Leighton Phillips, Dorset (GB)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 148 days.

(21) Appl. No.: 16/858,298

(22) Filed: Apr. 24, 2020

(65) Prior Publication Data
US 2021/0333204 A1    Oct. 28, 2021

(51) Int. Cl.
*G01N 21/3518*    (2014.01)
*G01N 33/00*    (2006.01)

(52) U.S. Cl.
CPC ..... *G01N 21/3518* (2013.01); *G01N 33/0047* (2013.01); *G01N 2201/0636* (2013.01)

(58) Field of Classification Search
CPC .......... G01N 21/3518; G01N 33/0047; G01N 2201/0636; G01N 2021/3137; G01N 2021/3148; G01N 2021/3166; G01N 21/314; G01N 2021/3513; G01N 21/3504; G01J 3/0208; G01J 3/021; G01J 3/427

See application file for complete search history.

(56) References Cited

U.S. PATENT DOCUMENTS

| | | | | |
|---|---|---|---|---|
| 3,562,524 A | * | 2/1971 | Moore | G01N 21/3504 250/343 |
| 3,916,195 A | * | 10/1975 | Burch | G01N 21/3518 250/345 |
| 5,262,645 A | * | 11/1993 | Lambert | G01N 21/3577 250/339.04 |
| 5,591,975 A | * | 1/1997 | Jack | G01N 33/0037 356/438 |
| 5,811,812 A | | 9/1998 | Williams et al. | |
| 6,201,245 B1 | * | 3/2001 | Schrader | G01N 21/3504 250/353 |
| 6,455,854 B1 | | 9/2002 | Richman | |
| 6,486,474 B1 | * | 11/2002 | Owen | G01N 21/031 250/339.02 |
| 6,853,452 B1 | * | 2/2005 | Laufer | G01N 21/3504 356/438 |

(Continued)

FOREIGN PATENT DOCUMENTS

| | | | | | |
|---|---|---|---|---|---|
| CN | 103913807 A | * | 7/2014 | | G01J 3/0208 |
| CN | 108801967 A | * | 11/2018 | | G01N 21/3518 |

(Continued)

OTHER PUBLICATIONS

Extended European search report dated Sep. 1, 2021 for EP Application No. 21167948, 7 pages.

*Primary Examiner* — Mohamed K Amara
(74) *Attorney, Agent, or Firm* — Alston & Bird LLP

(57) ABSTRACT

Methods, apparatuses, and systems for improving gas detecting devices are provided. An example gas detecting device may include a receiver element. In some examples, the receiver element may include a sample filter component and a reference filter component. In some examples, the sample filter component may be positioned coaxially with the reference filter component.

18 Claims, 14 Drawing Sheets

(56) References Cited

U.S. PATENT DOCUMENTS

| | | | |
|---|---|---|---|
| 9,207,170 B2 | 12/2015 | Tröllsch | |
| 9,506,804 B2 | 11/2016 | Lu et al. | |
| 10,768,101 B2* | 9/2020 | Schossig | G01N 21/3504 |
| 11,079,318 B2* | 8/2021 | Nemirovsky | G01N 21/314 |
| 2002/0011568 A1 | 1/2002 | Diekmann | |
| 2004/0256560 A1* | 12/2004 | Russell | G01N 21/3504 |
| | | | 250/338.5 |
| 2006/0263256 A1* | 11/2006 | Koshel | G01N 21/3504 |
| | | | 422/83 |
| 2007/0242720 A1* | 10/2007 | Eckles | G01J 3/0297 |
| | | | 372/107 |
| 2008/0149819 A1* | 6/2008 | Zhdaneev | G01N 33/2823 |
| | | | 250/255 |
| 2019/0154584 A1* | 5/2019 | Ahn | G01N 33/49 |

FOREIGN PATENT DOCUMENTS

| | | | | |
|---|---|---|---|---|
| CN | 105319703 B | * | 11/2019 | G01J 3/0208 |
| EP | 2169384 A1 | | 3/2010 | |
| EP | 3051274 A1 | * | 8/2016 | G01N 21/0303 |

\* cited by examiner

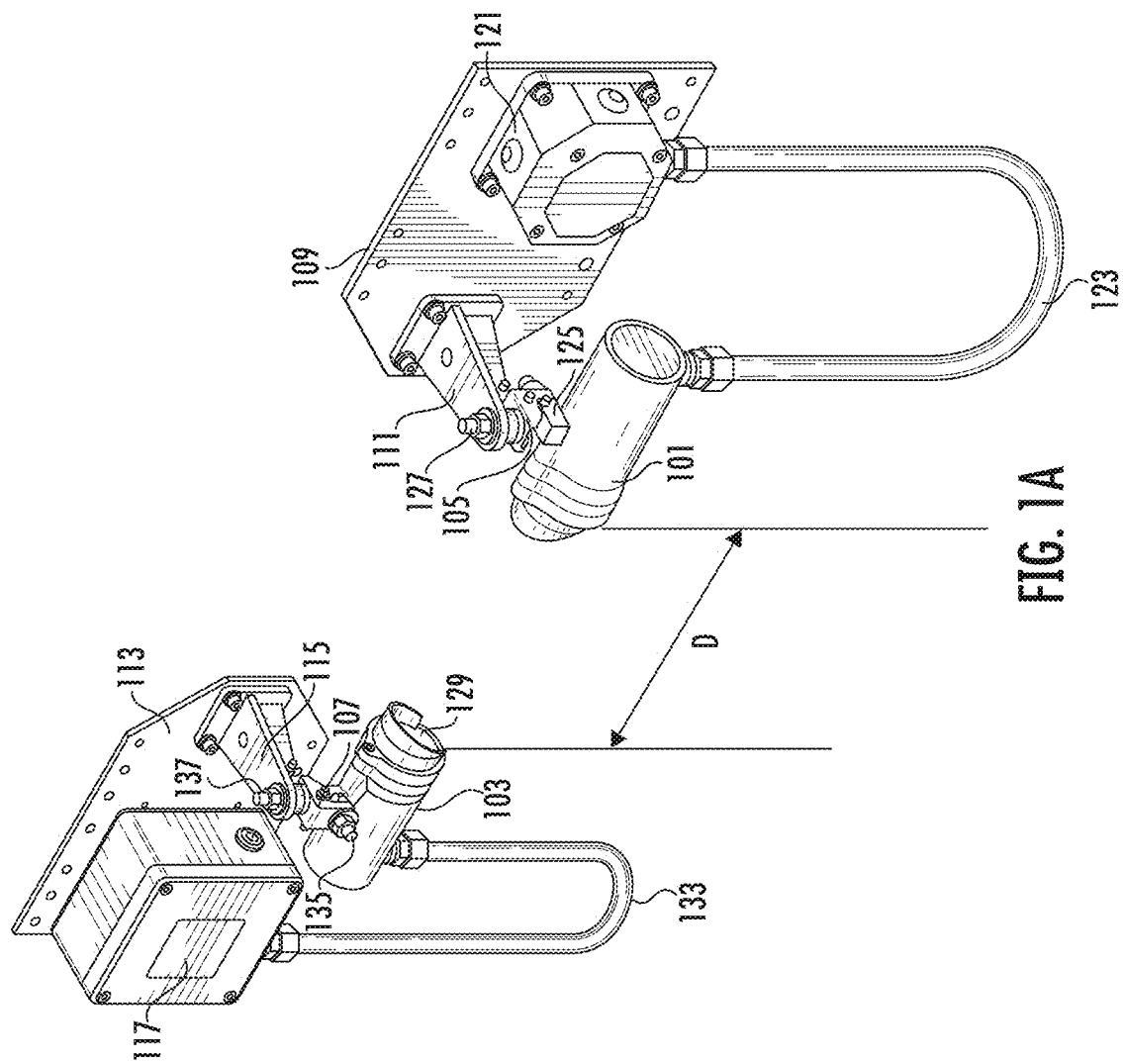

METHODS, APPARATUSES, AND SYSTEMS FOR IMPROVING GAS DETECTING DEVICES

BACKGROUND

A gas detecting device (or a gas detector) refers to an apparatus that may detect, measure, and/or identify one or more gaseous substances in an environment. For example, a gas detecting device may detect a concentration level of a gaseous substance (also referred to as "target gaseous substance") in an area. A gas detecting device may be part of a safety system. When the concentration level of hazardous or harmful gaseous substance detected by the gas detecting device exceeds a threshold, the safety system may generate a notification (for example, an alarm) to operator(s) of the safety system, so that the operator(s) may carry out one or more remedial actions (for example, shutting down the source of the gaseous substance, leaving the area, etc.).

BRIEF SUMMARY

In accordance with various examples of the present disclosure, an example gas detecting device may be provided.

In some examples, the example gas detecting device may comprise a receiver element. In some examples, the receiver element may comprise a sample filter component and/or a reference filter component. In some examples, the sample filter component may be positioned at a first coaxial arrangement relative to the reference filter component. For example, the sample filter component may be positioned coaxially with the reference filter component.

In some examples, the sample filter component may comprise a sample optical filter configured to pass a first portion of infrared light within a first wavelength range. In some examples, the reference filter component may comprise a reference optical filter configured to pass a second portion of the infrared light within at least one of a second wavelength range or a third wavelength range.

In some examples, the first wavelength range may be based at least in part on an absorption wavelength range associated with a target gaseous substance.

In some examples, the first wavelength range may at least partially overlap with the third wavelength range.

In some examples, the first wavelength range may be between the second wavelength range and the third wavelength range.

In some examples, the receiver element may further comprise a sample detector component and/or a reference detector component.

In some examples, the sample detector component may comprise a sample infrared light detector configured to generate a first light intensity indication corresponding to the first portion of the infrared light within the first wavelength range.

In some examples, the reference detector component may comprise a reference infrared light detector configured to generate a second light intensity indication corresponding to the second portion of the infrared light within at least one of the second wavelength range or the third wavelength range.

In some examples, the sample infrared light detector of the sample detector component may be positioned at a second coaxial arrangement relative to the sample optical filter of the sample filter component. For example, the sample infrared light detector may be positioned coaxially with the sample optical filter.

In some examples, the reference infrared light detector of the reference detector component may be positioned at a third coaxial arrangement relative to the reference optical filter of the reference filter component. For example, the reference infrared light detector may be positioned coaxially with the reference optical filter.

In some examples, the sample optical filter of the sample filter component may be positioned between the sample infrared light detector of the sample detector component and the reference infrared light detector of the reference detector component.

In some examples, the reference optical filter of the reference filter component may be positioned between the sample optical filter of the sample filter component and the reference infrared light detector of the reference detector component.

In some examples, the sample optical filter of the sample filter component, the sample infrared light detector of the sample detector component, the reference optical filter of the reference filter component, and the reference infrared light detector of the reference detector component may be positioned at a fourth coaxial arrangement relative to each other. For example, the sample optical filter, the sample infrared light detector, the reference optical filter, and the reference infrared light detector may be positioned coaxially with each other.

In some examples, the gas detecting device may further comprise a transmitter element. In some examples, the transmitter element may comprise an infrared light source component configured to generate infrared light on a first optical path at a first light direction. In some examples, the receiver element may be positioned on the first optical path at the first light direction.

In some examples, the receiver element may comprise a mirror component positioned on the first optical path at the first light direction and configured to direct the infrared light to a second optical path at a second light direction.

In some examples, the receiver element may comprise a sample detector component. In some examples, the sample filter component and the sample detector component may be positioned on the second optical path at the second light direction.

In some examples, the sample detector component may be positioned at a second coaxial arrangement relative to the sample filter component. For example, the sample detector component may be positioned coaxially with the sample filter component.

In some examples, the sample filter component may be configured to pass a first portion of the infrared light within a first wavelength range. In some examples, the sample detector component may be configured to generate a first light intensity indication corresponding to the first portion of the infrared light within the first wavelength range.

In some examples, the sample filter component may be configured to direct a second portion of the infrared light outside the first wavelength range to a third optical path at a third light direction.

In some examples, the receiver element may comprise a reference detector component. In some examples, the reference filter component and the reference detector component may be positioned on the third optical path at the third light direction.

In some examples, the reference detector component may be positioned at a second coaxial arrangement relative to the reference filter component. For example, the reference detector component may be positioned coaxially with the reference filter component.

In some examples, the reference filter component may be configured to pass a third portion of the infrared light within one of a second wavelength range or a third wavelength range. In some examples, the reference detector component may be configured to generate a second light intensity indication corresponding to the third portion of the infrared light within one of the second wavelength range or the third wavelength range.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative examples may be read in conjunction with the accompanying figures. It will be appreciated that, for simplicity and clarity of illustration, components and elements illustrated in the figures have not necessarily been drawn to scale, unless described otherwise. For example, the dimensions of some of the components or elements may be exaggerated relative to other elements, unless described otherwise. Examples incorporating teachings of the present disclosure are shown and described with respect to the figures presented herein, in which:

FIG. 1A illustrates an example view of an example open path gas detecting device in accordance with various examples of the present disclosure;

DETAILED DESCRIPTION OF THE INVENTION

Figure 1C:
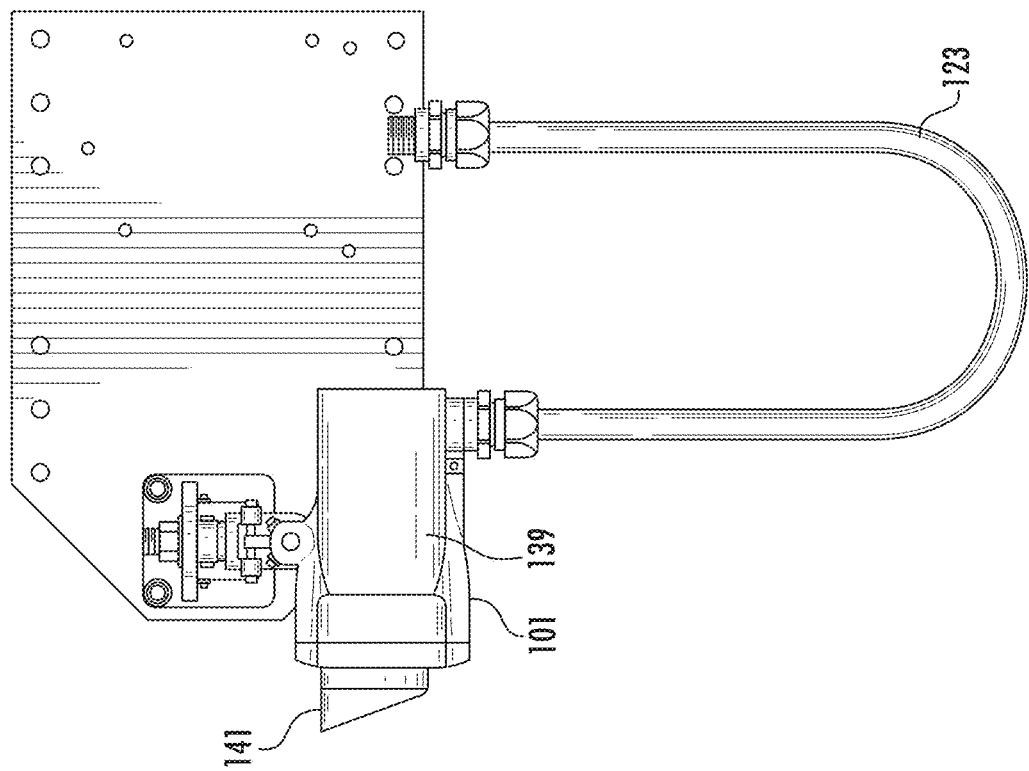
FIG. 1B and FIG. 1C illustrate example views of an example transmitter element in accordance with various examples of the present disclosure.

Some examples of the present disclosure will now be described more fully hereinafter with reference to the accompanying drawings, in which some, but not all examples of the disclosure are shown. Indeed, these disclosures may be embodied in many different forms and should not be construed as limited to the examples set forth herein; rather, these examples are provided so that this disclosure will satisfy applicable legal requirements. Like numbers refer to like elements throughout.

The phrases "in one example," "according to one example," "in some examples," and the like generally mean that the particular feature, structure, or characteristic following the phrase may be included in at least one example of the present disclosure and may be included in more than one example of the present disclosure (importantly, such phrases do not necessarily refer to the same example).

If the specification states a component or feature "may," "can," "could," "should," "would," "preferably," "possibly," "typically," "optionally," "for example," "as an example," "in some examples," "often," or "might" (or other such language) be included or have a characteristic, that specific component or feature is not required to be included or to have the characteristic. Such component or feature may be optionally included in some examples, or it may be excluded.

The word "example" or "exemplary" is used herein to mean "serving as an example, instance, or illustration." Any implementation described herein as "exemplary" is not necessarily to be construed as preferred or advantageous over other implementations.

The term "electronically coupled," "electronically coupling," "electronically couple," "in communication with," "in electronic communication with," or "connected" in the present disclosure refers to two or more elements or components being connected through wired means and/or wireless means, such that signals, electrical voltage/current, data and/or information may be transmitted to and/or received from these elements or components.

Various examples of the present disclosure may provide example technical improvements on the performance of gas detecting devices. One example of a gas detecting device is as an "open path gas detecting device," which refers to a type of gas detectors that may be configured to detect, measure, and/or identify a concentration level of one or more gaseous substances ("target gaseous substance") in an area and/or along a path. In some examples, the open path gas detecting device may be based on a spectroscopic sensor such as a nondispersive infrared (NDIR) sensor. For example, an example open path gas detecting device may comprise at least two elements: a transmitter element and a receiver element. The transmitter element may be positioned at a distance from the receiver element, forming an optical path between the transmitter element and the receiver element.

The transmitter element may be configured to emit infrared light (also referred to as infrared radiation herein). The infrared light may travel along the optical path between the transmitter element and the receiver element, and gaseous substance along the optical path may absorb at least some of infrared light. The infrared light may ultimately be received and detected by the receiver element. The receiver element may comprise at least one filter component and at least one detector component. In some examples, the at least one filter component may filter the received infrared light at one or more wavelengths, and may direct the infrared light to the at least one detector component. In some examples, the at least one detector component may detect, measure, and/or identify the intensity level of the infrared light at the one or more wavelengths filtered by the at least one filter component. For example, the at least one detector component may comprise a sensor that may comprise a photodiode active area to detect, measure, and/or identify intensity level of the infrared light. Additionally, or alternatively, other suitable sensor(s) may be implemented to detect, measure, and/or identify the intensity level of the infrared light or the infrared radiation.

Based on the intensity level of the infrared light as detected by receiver element, the open path gas detecting device may calculate the level of infrared light that has been absorbed by the gaseous substance along the optical path, and therefore may, in some examples, determine the concentration level of the gaseous substance. Additional details of the open path gas detecting device, the transmitter element, and the receiver element are described further herein.

Referring now to FIG. 1A, FIG. 1B, FIG. 1C, FIG. 1D, and FIG. 1E, example views of example components of an example open path gas detecting device are illustrated. In the example shown in FIG. 1A, the example open path gas detecting device may comprise a transmitter element 101 and a receiver element 103.

In some examples, the transmitter element 101 may be configured to produce, generate, emit, and/or trigger the production, generation, and/or emission of infrared light. For example, the transmitter element 101 may comprise an infrared light source component that may produce, generate, and/or emit infrared light. Example infrared light source components may include, but are not limited to, gas discharge lamps, fluorescent lamps, heat lamps, and/or the like. The term "gas discharge lamp" refers to a type of artificial light source that may generate light by sending an energy discharge (such as electric discharge) through an ionized gas. As an example, the infrared light source component of the transmitter element 101 may comprise a xenon arc flashlamp. An example xenon arc flashlamp may produce, generate, and/or emit beams of light by discharging electricity through ionized xenon gas, and the light produced, generated, and/or emitted by the xenon arc flashlamp may comprise infrared light.

While the above description illustrates a xenon arc flashlamp as an example infrared light source component, it is noted that the scope of the present disclosure is not limited to xenon arc flashlamps. Additionally, or alternatively, examples of the present disclosure may implement other type(s) of infrared light source component(s) for producing infrared light.

In some examples, the infrared light may be produced at an intense level by the infrared light source component of the transmitter element 101. In some examples, the infrared light source component may be electronically coupled to a power source component, and the power source component may supply power to the infrared light source component to generate discharge energy for triggering infrared light. For example, the example xenon arc flashlamp may produce infrared light that has a pulse frequency of 4 Hz, and each pulse of infrared light may have a duration of approximately one microsecond. The pulse frequency, extremely short duration of these pulses of light, and/or the shape of the discharge pulses may distinguish the infrared light generated by the xenon arc flashlamp from other natural and artificial sources of infrared light in the environment. As a result, the receiver element 103 may detect, measure, and/or identify infrared light produced by the xenon arc flashlamp of the transmitter element 101.

While the above description illustrates example pulse frequency and duration of the infrared light generated by an example xenon arc flashlamp, it is noted that the scope of the present disclosure is not limited to these examples only. For example, examples of the present disclosure may include infrared light produced at a pulse frequency higher than or lower than 4 Hz. Additionally, or alternatively, examples of the present disclosure may include infrared light that have a duration of less than or more than one microsecond.

In some examples, the infrared light produced by the infrared light source component may be collimated. For example, the transmitter element 101 may comprise one or more optical components (such as optical collimating lens) to redirect and/or adjust the direction of the infrared light generated by the infrared light source component. As a result, parallel beams of infrared light may be emitted from the transmitter element 101 through the infrared light source component and the one or more optical components.

Figure 1B:
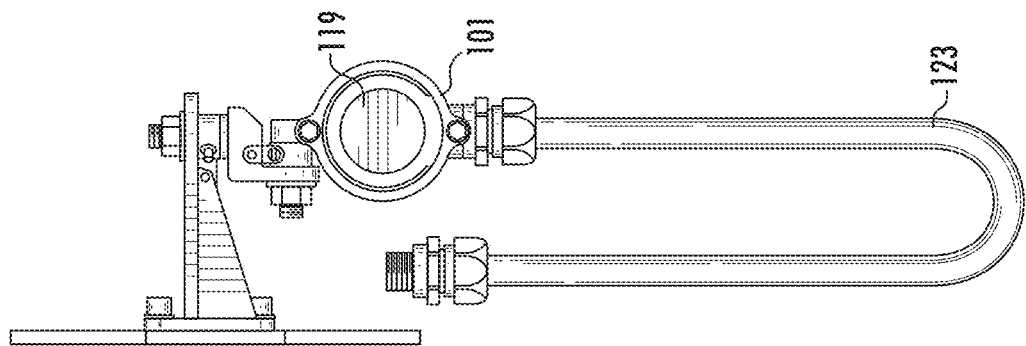

Referring now to FIG. 1B and FIG. 1C, a front view and a side view of the transmitter element 101 are illustrated, respectively.

In the example shown in FIG. 1C, the transmitter element 101 may comprise a housing 139, which may provide an enclosure for various components of the transmitter element 101 (for example, an infrared light source component and one or more optical components described above). In some examples, the transmitter element 101 may comprise a conduit component 123. The conduit component 123 may be connected to the transmitter element 101, which may provide a protective enclosure for electrical wire(s) that may connect components within the housing 139 (for example, an infrared light source component) with components that are outside of housing 139 (for example, a power source component).

In the example shown in FIG. 1B, infrared light generated by the infrared light source component may pass through the window lens component 119. In some examples, the window lens component 119 may comprise glass and/or other transparent material that may allow the infrared light to pass through. In some examples, the window lens component 119 may be heated to minimize condensation, frosting and/or buildup of snow. In some examples, the transmitter element 101 may comprise an awning component (for example, the awning component 141 as shown in FIG. 1C) that may protect the window lens component 119 from rain, snow, and/or other particles that may fall on the window lens component 119.

Referring back to FIG. 1A, the transmitter element 101 may be connected to an mounting bracket 111 through a pivot block 105. As an example, the transmitter element 101 may be connected to the pivot block 105 through a fastener 125 (such as a bolt and a nut). As an example, the pivot block 105 may be fastened to the mounting bracket 111 through a fastener 127 (such as a bolt and a nut). Prior to the fastener 125 and the fastener 127 being tightened, the transmitter element 101 may rotate to a desired angle, such that the transmitter element 101 may align with the receiver element 103. For example, prior to the fastener 125 being tightened, the transmitter element 101 may rotate around a horizontal axis. Prior to the fastener 127 being tightened, the pivot block 105 may rotate around a vertical axis, which may in turn cause the transmitter element 101 to rotate around the vertical axis.

While the above description illustrates example structural connections and relationships between the transmitter element 101 and various other components of the example open path gas detecting device, it is noted that the scope of the present disclosure is not limited to these example structural connections and relationships only. Additionally, or alternatively, the transmitter element 101 may be connected and/or fastened to other components of the example open path gas detecting device through other means or in other ways.

Referring back to FIG. 1A, the mounting bracket 111 may be fastened to the mounting plate 109 through one or more fasteners (such as screws), and the mounting plate 109 may be fastened to a secured structure (for example, a wall) through one or more fasteners (such as screws).

In the example shown in FIG. 1A, a junction box component 121 may be securely fastened to the mounting plate 109. The junction box component 121 may provide a protective enclosure for various components of the open path gas detecting device (such as a power source component, electric circuits including processing circuitry (such as a microcontroller), memory circuitry, and/or the like). In some examples, the conduit component 123 may be connected to the transmitter element 101 and the junction box component 121, and one or more components within the junction box component 121 may be connected to components within the transmitter element 101 through electrical wire(s) that are disposed within the conduit component 123, as described above.

In some examples, the receiver element 103 may be configured to detect, measure, and/or identify the intensity level of the infrared light. The infrared light generated by the transmitter element 101 may travel through an optical path between the transmitter element 101 and the receiver element 103 (for example, the optical path D as shown in FIG. 1A). In some examples, the distance of the optical path D (for example, the distance between the window lens component 129 of the receiver element and the window lens component 119 of the transmitter element 101) may be between 5 meters to 350 meters. In some examples, the distance of the optical path D may have other values.

Figure 1E:
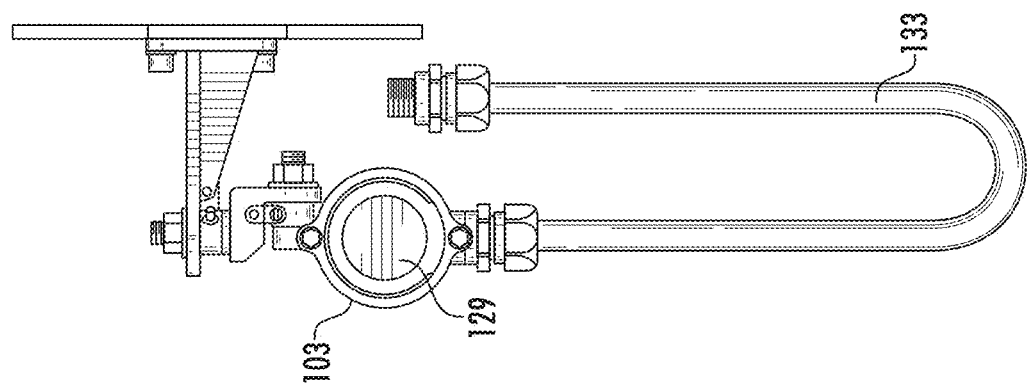
FIG. 1D and FIG. 1E illustrate example views of an example receiver element in accordance with various examples of the present disclosure.
Figure 1D:
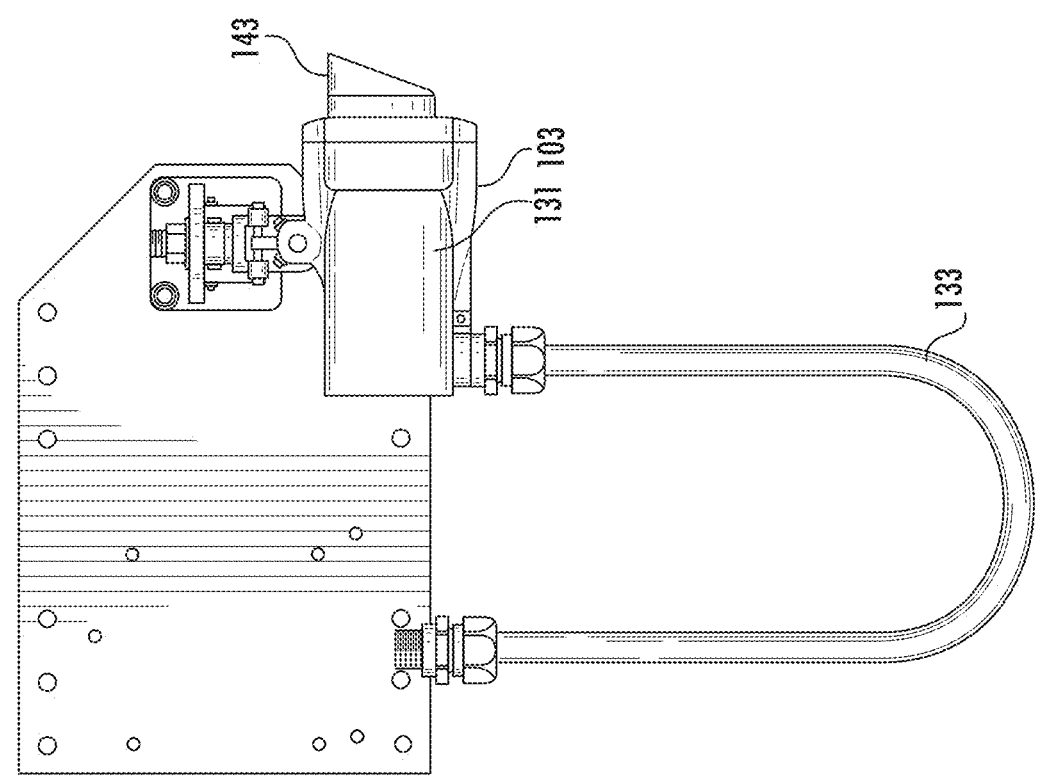

Referring now to FIG. 1D and FIG. 1E, a side view and a front view of the receiver element 103 are illustrated, respectively.

As described above, gaseous substance along the optical path D may absorb at least some of the infrared light transmitted by the transmitter element 101. The infrared light may travel through the window lens component 129 of the receiver element 103, and the receiver element 103 may comprise at least one detector component to detect, measure, and/or identify the absorption level of the infrared light by the gaseous substance along the optical path D. Based on the absorption level, the open path gas detecting device may detect, measure, and/or identify the concentration level of the gaseous substance.

In some examples, the receiver element 103 may comprise a sample detector component and a reference detector component. In some examples, the receiver element 103 may comprise an optical component that may divide the infrared light into two or more portions (for example, but not limited to, a beam splitter component, a selective filter component (for example, a selective bandpass filter).

In some examples, at least a portion of the infrared light may travel through a sample filter component and arrive at the sample detector component. As described above, the gaseous substance to be detected ("target gaseous substance") may absorb at least some of the infrared light, and the sample filter component may filter the infrared light at wavelength(s) and/or wavelength(s) ranges where the target gaseous substance may absorb the infrared light. Accordingly, the sample detector component may detect the intensity level of infrared light at such wavelength(s) and/or wavelength(s) ranges where target gaseous substance may absorb the infrared light.

In some examples, at least a portion of the infrared light may travel through a reference filter component and arrive at the reference detector component. The reference filter component may filter the infrared light at wavelength(s) and/or wavelength(s) ranges where the target gaseous substance may not or may be less likely to absorb the infrared light. Accordingly, the reference detector component may detect the intensity level of infrared light at such wavelength(s) and/or wavelength(s) ranges where target gaseous substance may not or may be less likely to absorb the infrared light.

In some examples, by calculating a difference or ratio value between the intensity level of infrared light detected by the sample detector component and the intensity level of infrared light detected by the reference detector component, the example open path gas detecting device may determine the concentration level of target gaseous substance along the optical path D.

In the example shown in FIG. 1D and FIG. 1E, the receiver element 103 may comprise a housing 131, which may provide an enclosure for various components of the receiver element 103 (for example, the sample detector component, the sample filter component, the reference detector component, and the reference filter component described above).

In some examples, the receiver element 103 may comprise a conduit component 133. The conduit component 133 may be connected to the receiver element 103, which may provide a protective enclosure for electrical wire(s) that may connect components within the housing 131 (for example, the sample detector component, the reference detector component) with components that are outside of housing 131. For example, the sample detector component and the reference detector component may be connected to various electronic components to amplify, condition and/or process the signals received by the sample detector component and the reference detector component. As an example, the sample detector component and/or the reference detector component may be connected to a digital signal processor (DSP), which may be configured to perform signal processing calculations.

Additionally, or alternatively, a microprocessor may be implemented to control the overall function of the open path gas detecting device. For example, the microprocessor may be electronically coupled to the transmitter element 101 and/or the receiver element 103, and may perform the final calculations to determine reading of the concertation level of the target gaseous substance, and may output state of the open path gas detecting device.

Referring back to FIG. 1D and FIG. 1E, infrared light may travel through the window lens component 129 of the receiver element 103. In some examples, the window lens component 129 may be heated to minimize condensation, frosting and/or buildup of snow. In some examples, the level of heating applied to the window lens component 129 may be controlled by the microcontroller, and may be adjusted from zero to maximum depending on the temperature of the window lens component 129. In some examples, the receiver element 103 may comprise an awning component (for example, the awning component 143 as shown in FIG. 1D) that may protect the window lens component 129.

Referring back to FIG. 1A, the receiver element 103 may be connected to an mounting bracket 115 through a pivot block 107. As an example, the receiver element 103 may be connected to the pivot block 107 through a fastener 135 (such as a bolt and a nut). As an example, the pivot block 107 may be fastened to the mounting bracket 115 through a fastener 137 (such as a bolt and a nut). Prior to the fastener 135 and the fastener 137 being tightened, the receiver element 103 may rotate to a desired angle, such that the receiver element 103 may align with the transmitter element 101. For example, prior to the fastener 135 being tightened, the receiver element 103 may rotate around a horizontal axis. Prior to the fastener 137 being tightened, the pivot block 107 may rotate around a vertical axis, which may in turn cause the receiver element 103 to rotate around the vertical axis.

While the above description illustrates example structural connections and relationships between the receiver element 103 and various other components of the example open path gas detecting device, it is noted that the scope of the present disclosure is not limited to these example structural connections and relationships only. Additionally, or alternatively, the receiver element 103 may be connected and/or fastened to other components of the example open path gas detecting device through other means or in other ways.

Referring back to FIG. 1A, the mounting bracket 115 may be fastened to the mounting plate 113 through one or more fasteners (such as screws), and the mounting plate 113 may be fastened to a secured structure (for example, a wall) through one or more fasteners (such as screws).

In the example shown in FIG. 1A, a junction box component 117 may be securely fastened to the mounting plate 113. The junction box component 117 may provide a protective enclosure for various components of the open path gas detecting device (such as electronic components describe above). In some examples, the conduit component 133 may be connected to the receiver element 103 and the junction box component 117, and one or more components within the junction box component 117 may be connected to components within the receiver element 103 through electrical wire(s) that are disposed within the conduit component 133, as described above.

While the above description and FIGS. 1A-1E illustrate various example components of an example open path gas detecting device, it is noted that the scope of the present disclosure is not limited to these example components only. In some examples, an example open path gas detecting device may comprise less than or more than these example components as illustrated in FIGS. 1A-1E. Additionally, or alternatively, an example open path gas detecting device may comprise other components, including but not limited to, aimer, viewfinder, and/or the like.

As described above, an example receiver element of an open path gas detecting device may utilize two or more wavelength(s) and/or wavelength range(s). For example, infrared light within one wavelength/wavelength range (also referred to as sample wavelength or sample wavelength range) may primarily be absorbed by the target gaseous substance. Infrared light within another wavelength/wavelength range (also referred to as reference wavelength or reference wavelength range) may largely be unaffected by the target gaseous substance. The difference or ratio between intensity level of infrared light detected through these wavelength(s) and/or wavelength range(s) may be a function of the concentration level of target gaseous substance along the optical path.

Many applications of a gas detecting device may require a normalized or uniformed response to hydrocarbon gaseous substances (for example, methane, ethane, propane, butane, and/or the like). Without a normalized or uniformed response to different hydrocarbon gaseous substances, customers are required, in some examples, to determine which gaseous substance they wish a gas detecting device to be calibrated for, which may lead to significant complexity in the specification, sourcing, and maintenance of gas detecting devices. Additionally, in many applications, multiple hydrocarbon gaseous substances are present and, consequently, a particular gas detecting device may either under read or over read in response to the mixed gaseous substances other than the specific gaseous substance it was calibrated to detect.

In some examples, a normalized response to hydrocarbon gaseous substance may depend upon the design of the receiver element to produce similar ratio values between wavelength(s) and/or wavelength range(s) of infrared light that pass through the sample filter component and/or the reference filter component and the absorption wavelength(s) and/or wavelength range(s) of different hydrocarbon gaseous substances at the target concentration level(s).

Additionally, or alternatively, the sensitivity of a gas detecting device to the target gaseous substance may need to be higher than the sensitivity of the gas detecting device to other substances that are not target gaseous substance (for example, water, fog, mist). For example, a gas detecting device may need to increase throughput to maintain the performance of gas detecting device through a dense fog condition. As such, the overlap(s) between the wavelength(s) and/or wavelength range(s) of infrared light that pass through the sample filter component and the absorption wavelength(s) and/or wavelength range(s) of infrared light by the target gaseous substance may need to be as large as practical, while the wavelength(s) and/or wavelength range(s) of infrared light that may pass through the reference filter component and the absorption wavelength(s) and/or wavelength range(s) of infrared light by the target gaseous substance may need to be as small as practical.

In some examples, to increase throughput, the sample filter component and/or the reference filter component may need to function over large angles of incidence, which may cause excessive demands on the control of filter parameters, such as peak transmission amplitude and full width at half maximum (FWHM) bandwidths. In some examples, to minimize sensitivity to water, fog, and mist, the wavelength(s) and/or wavelength range(s) of infrared light that may pass through the sample filter component and/or the reference filter component may need to have little or no overlap with the absorption wavelength(s) and/or wavelength range(s) of infrared light by water and water vapor.

In accordance various examples of the present disclosure, an example receiver element may, for example, maximize throughput while providing a normalized response to hydrocarbon gaseous substance(s) as discussed above. For example, examples of the present disclosure may utilize both the transmissive and reflective properties of sample filter component and/or reference filter component in a coaxial arrangement to enable a selection of wavelength(s) or wavelength range(s) of infrared light.

Figure 2:
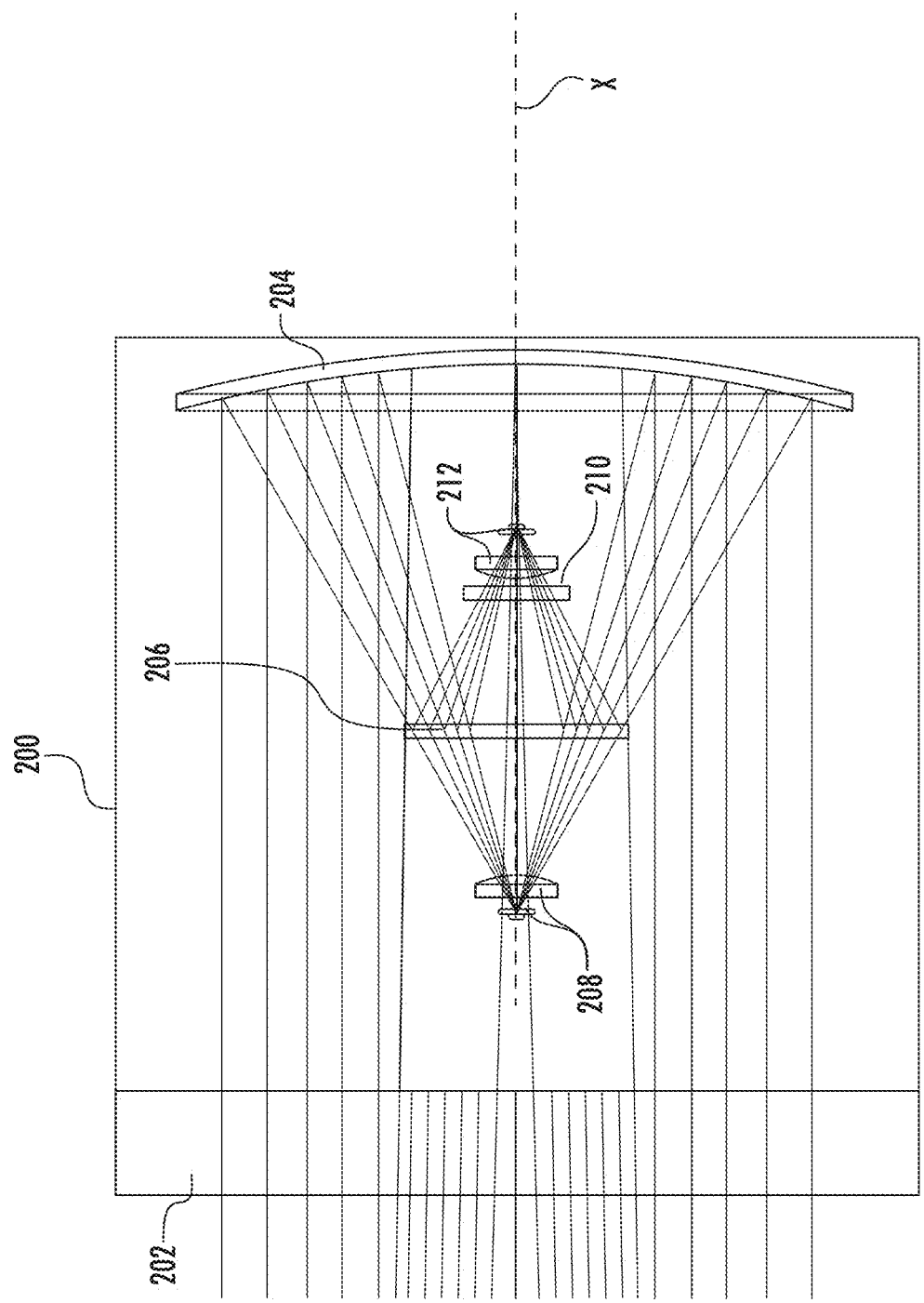
FIG. 2 illustrates an example diagram of at least some example components of an example receiver element in accordance with various examples of the present disclosure.

Referring now to FIG. 2, an example diagram illustrating various components of an example receiver element 200 of an example open path gas detecting device is shown.

As described above, the example receiver element 200 may comprise various components for detecting, measuring, and/or identifying an intensity level of the infrared light received by the receiver element 200. For example, the receiver element 200 may receive infrared light that is generated by an example transmitter element of an example open path gas detecting device, and the infrared light may travel through the optical path and the window lens component 202 of the receiver element 200. The infrared light may be redirected by a mirror component 204. In some examples, the receiver element 200 may comprise a sample detector component 208 and a reference detector component 212.

In some examples, at least a portion of the infrared light may travel through a sample filter component 206 and arrive at the sample detector component 208. As described above, the target gaseous substance may absorb infrared light, and the sample filter component 206 may filter the infrared light at wavelength(s) and/or wavelength(s) ranges where the target gaseous substance may absorb the infrared light. Accordingly, the sample detector component 208 may detect the intensity level of infrared light at such wavelength(s) and/or wavelength(s) ranges where target gaseous substance may absorb the infrared light, and may generate a light intensity indication indicating such intensity level.

In some examples, at least a portion of the infrared light may travel through a reference filter component 210 and arrive at the reference detector component 212. The reference filter component 210 may filter the infrared light at wavelength(s) and/or wavelength(s) ranges where the target gaseous substance may not or may be less likely to absorb the infrared light. Accordingly, the reference detector component 212 may detect the intensity level of infrared light at such wavelength(s) and/or wavelength(s) ranges where target gaseous substance may not or may be less likely to absorb the infrared light, and may generate a light intensity indication indicating such intensity level.

In some examples, by calculating a difference or ratio value between the intensity level of infrared light detected by the sample detector component 208 and the intensity level of infrared light detected by the reference detector component 212, the example open path gas detecting device may determine the concentration level of target gaseous substance along the optical path. In some examples, the example receiver element 200 may transmit data and/or signal associated with the concentration level of target gaseous substance to a connected control system (for example, to a processing circuitry such as a microcontroller). In some examples, the example receiver element 200 may implement functionality, in some examples, for installation, commissioning, and maintenance of the open path gas detecting device.

In some examples, the sample filter component 206, the sample detector component 208, the reference filter component 210, and the reference detector component 212 may be disposed within the receiver element 200. For example, each of the sample filter component 206, the sample detector component 208, the reference filter component 210, and the reference detector component 212 may be securely positioned with respect an inner surface of the receiver element 200 through one or more supporting beams and/or other supporting structure.

In some examples, the sample filter component 206 may be positioned between the sample detector component 208 and the reference detector component 212. For example, the sample filter component 206 may comprise a sample optical filter (also referred to as "sample optical lens" herein); the sample detector component 208 may comprise a sample infrared light detector; and the reference detector component 212 may comprise a reference infrared light detector (details of which are described herein). In such an example, the sample optical filter of the sample filter component 206 may be positioned between the sample infrared light detector of the sample detector component 208 and the reference infrared light detector of the reference detector component 212.

In some examples, the reference filter component 210 may be positioned between the sample filter component 206 and the reference detector component 212. For example, a reference optical filter (also referred to as "reference optical lens" herein) of the reference filter component 210 may be positioned between the sample optical filter of the sample filter component 206 and the reference infrared light detector of the reference detector component 212.

In some examples, the sample filter component 206 may be positioned at a coaxial arrangement relative to the reference filter component 210. In some examples, the sample filter component 206 may be positioned coaxially with the reference filter component 210. For example, an optical axis X may pass through the center of the sample filter component 206 and the center of the reference filter component 210.

In some examples, the sample filter component 206, the sample detector component 208, the reference filter component 210, and the reference detector component 212 may be positioned in a coaxial arrangement or coaxially with one another. For example, an optical axis X may pass through the center of the sample filter component 206, the center of the sample detector component 208, the center of the reference filter component 210, and the center of the reference detector component 212. In some examples, the sample optical filter of the sample filter component 206, the sample infrared light detector of the sample detector component 208, the reference optical filter of the reference filter component 210, and the reference infrared light detector of the reference detector component 212 are positioned at a fourth coaxial arrangement relative to or coaxially with each other.

While the above description illustrates some example components of the receiver element 200, it is noted that the scope of the present disclosure is not limited to these example components only. For example, an example receiver element may additionally or alternatively include other components, and/or various components of the receiver element may be positioned differently than those shown in FIG. 2.

Figure 3:
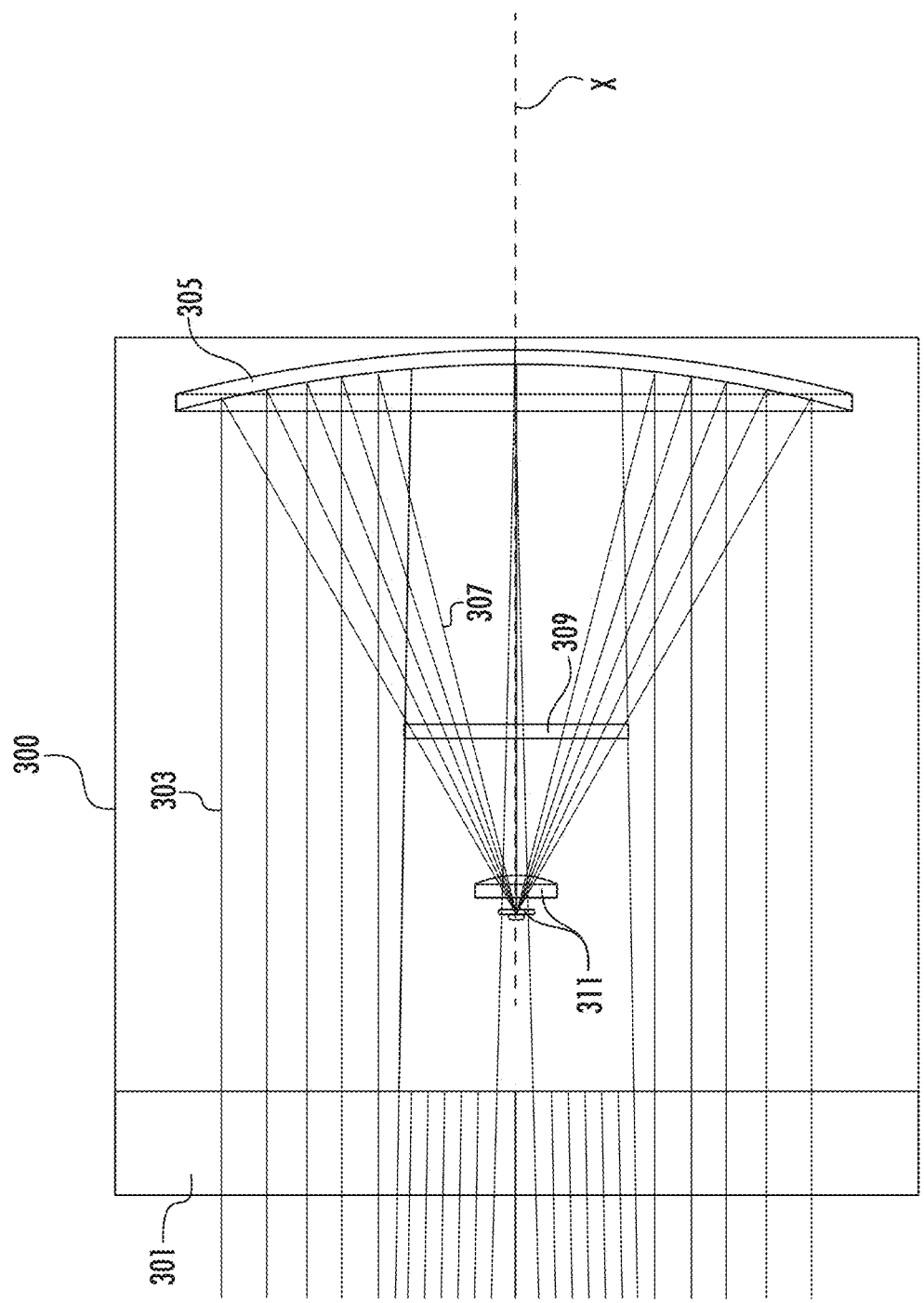
FIG. 3 illustrates an example diagram of at least some example components of an example receiver element in accordance with various examples of the present disclosure.

Referring now to FIG. 3, an example diagram of at least some example components of an example receiver element 300 in accordance with various examples of the present disclosure is illustrated.

In some examples, the receiver element 300 may receive and/or detect infrared light. In some examples, the infrared light may be generated by a transmitter element. For example, the transmitter element may comprise an infrared light source component configured to generate infrared light. The infrared light may be emitted from the transmitter element, and may travel along an optical path between the transmitter element and the receiver element 300.

In the example shown in FIG. 3, the infrared light may travel on a first optical path 303 at a first light direction. In such an example, the receiver element 300 may be positioned on the first optical path 303 at the first light direction, such that the infrared light may be received by the receiver element 300.

In some examples, the receiver element 300 may comprise a window lens component 301. In some examples, the infrared light may pass through the window lens component 301. In some examples, the window lens component 301 may comprise a transparent material, such as but not limited to, glass.

In some examples, the receiver element 300 may comprise a mirror component 305. In some examples, the mirror component 305 may comprise a reflective surface that may reflect and/or redirect light. For example, the mirror component 305 may comprise a piece of glass coated with a thin layer of metal, such as but not limited to silver or aluminum.

In some examples, the mirror component 305 may be positioned on the first optical path 303 at the first light direction. In some examples, the mirror component 305 may be configured to direct the infrared light to a second optical path 307 at a second light direction.

In some examples, the receiver element 300 may comprise a sample filter component 309. The sample filter component 309 may comprise a sample optical filter configured to pass a first portion of infrared light within a first wavelength range. For example, the sample optical filter may comprise material(s) such as silicon dioxide, sapphire, and/or the like. Additionally, or alternatively, one or more layers of chemical coatings may be applied on one or more surface(s) the sample optical filter, such that the sample optical filter may provide the desired transmissive characteristics.

In some examples, the receiver element 300 may comprise a sample detector component 311. In some examples, the sample detector component 311 may comprise a sample infrared light detector. For example, a surface of the sample infrared light detector may comprise a photodiode active area that may be configured to detect, measure, and/or identify intensity level of the infrared light. In some examples, the photodiode active area may comprise indium gallium arsenide (InGaAs). Additionally, or alternatively, the sample detector component 311 may comprise other suitable infrared detecting device.

In some examples, the sample filter component 309 and the sample detector component 311 may be positioned on the second optical path 307 and/or at the second light direction. For example, as shown in FIG. 3, infrared light (reflected from the mirror component 305) may travel on the second optical path 307 at the second light direction through the sample optical filter of the sample filter component 309, and may be received by the sample infrared light detector of the sample detector component 311.

In the example shown in FIG. 3, the sample detector component 311 may be positioned at a coaxial arrangement relative to or positioned coaxially with the sample filter component 309. For example, the sample infrared light detector of the sample detector component 311 may be positioned at a coaxial arrangement relative to or positioned coaxially with the sample optical filter of the sample filter component 309, such that an optical axis X may pass through the center of the sample infrared light detector and the center of the sample optical filter. In some examples, a surface of the sample optical filter may be in a perpendicular arrangement with the optical axis X. In some examples, a surface of the sample infrared light detector (for example, a surface that comprises a photodiode active area) may be in a perpendicular arrangement with the optical axis X.

As described, the sample filter component 309 is configured to pass a first portion of the infrared light within a first wavelength range. Accordingly, the sample detector component 311 may be configured to generate a first light intensity indication corresponding to the first portion of the infrared light within the first wavelength range that has passed through the sample filter component 309.

In some examples, the mirror component 305, the sample filter component 309, and the sample detector component 311 may be disposed within the receiver element 300. For example, each of the mirror component 305, the sample filter component 309, and the sample detector component 311 may be securely positioned with respect an inner surface of the receiver element 300 through one or more supporting beams and/or other supporting structure.

Figure 4:
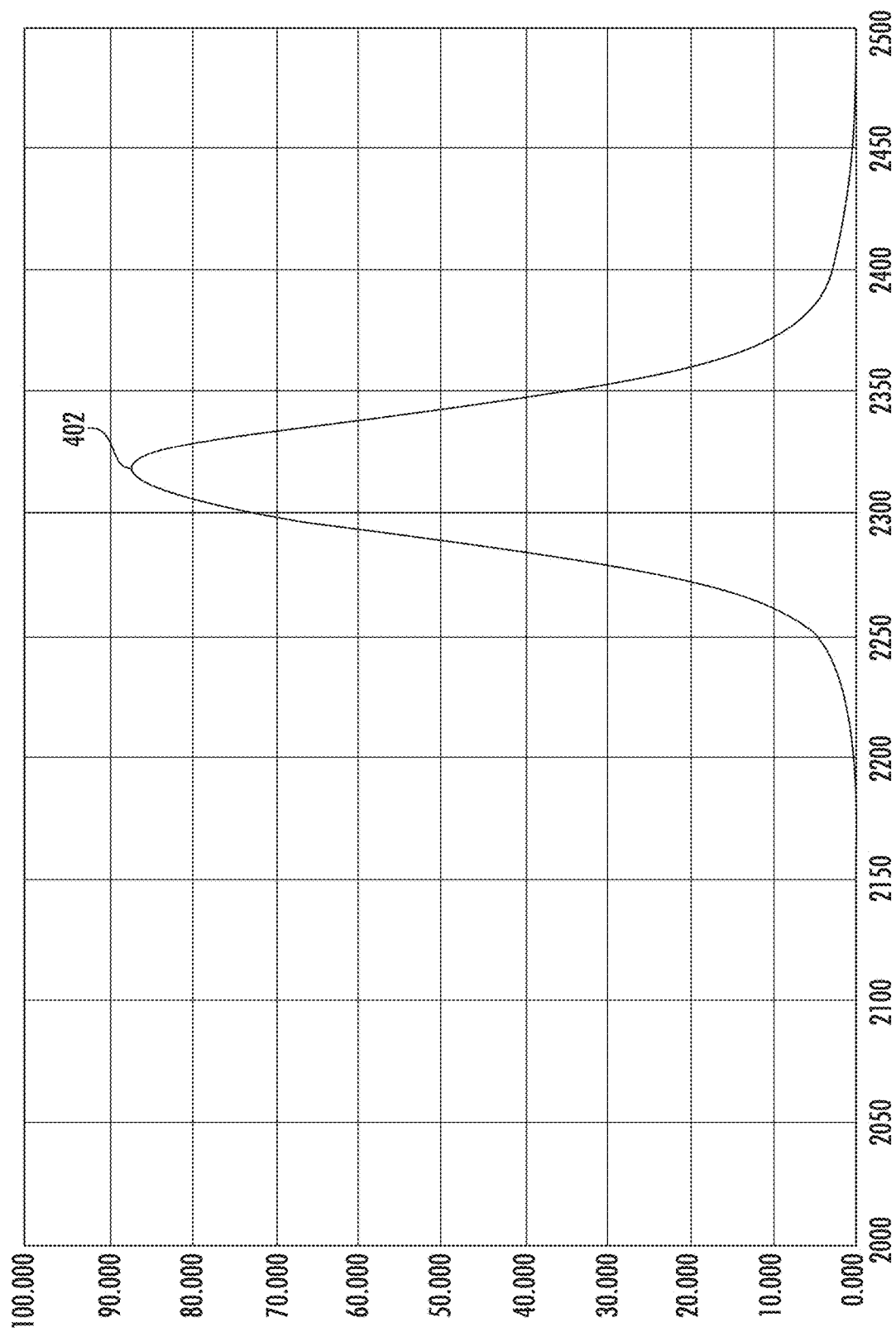
FIG. 4 illustrates an example diagram showing example wavelength range(s) associated with an example sample filter component in accordance with examples of the present disclosure.

Referring now to FIG. 4, an example diagram showing example wavelength range(s) associated with an example sample filter component in accordance with examples of the present disclosure is illustrated. For example, the example diagram may illustrate example intensity levels associated with different wavelengths as detected by an example sample detector component based on infrared light that has passed through an example sample filter component. In other words, FIG. 4 illustrates example transmission characteristics of an example sample filter component.

As described, the sample filter component may comprise a sample optical filter configured to pass a first portion of infrared light within a first wavelength range. In the example shown in FIG. 4, the first wavelength range may be centered around the peak 402. In some examples, the center wavelength corresponding to the peak 402 may be between 2300 nanometers and 2350 nanometers (for example, 2315 nanometers). In some examples, the wavelength range associated with the center wavelength may have a full width at half maximum (FWHM) value between 40 nanometers and 80 nanometers (for example, 60 nanometers). In some examples, the peak transmission range of the example sample filter component may be between 70% and 90% (for example, 80%).

As described above, the sample filter component may filter the infrared light at wavelength(s) and/or wavelength(s) ranges where the target gaseous substance may absorb the infrared light. As such, the first wavelength range may be based at least in part on an absorption wavelength range associated with one or more target gaseous substances for the gas detecting device. As an example, the center wavelength and the FWHM value may be determined based on the absorption spectra associated with hydrocarbon gaseous substance(s). For example, the center wavelength may correspond to a peak absorption wavelength of one of the hydrocarbon gaseous substances, and the FWHM value may be determined such that the first wavelength range may cover peak absorption wavelength(s) of one or more hydrocarbon gaseous substance(s).

While the above description provides some example values associated with the wavelength range and the sample filter component, as well as methods for determining such example values, it is noted that that the scope of the present disclosure is not limited to these example values and example methods. In some examples, the wavelength range and/or the sample filter component may be associated with other values and/or determined through other means.

Figure 6:
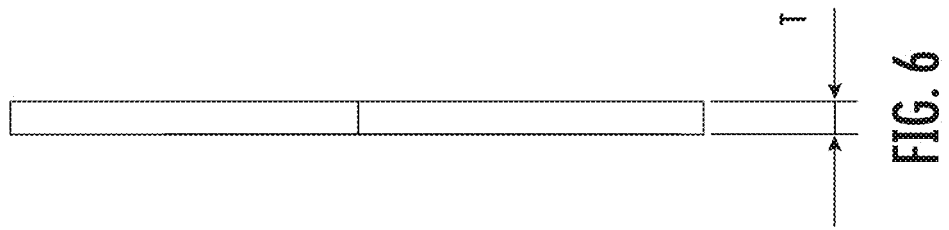
FIG. 6 illustrates an example side view of an example sample optical filter in accordance with examples of the present disclosure.
Figure 5:
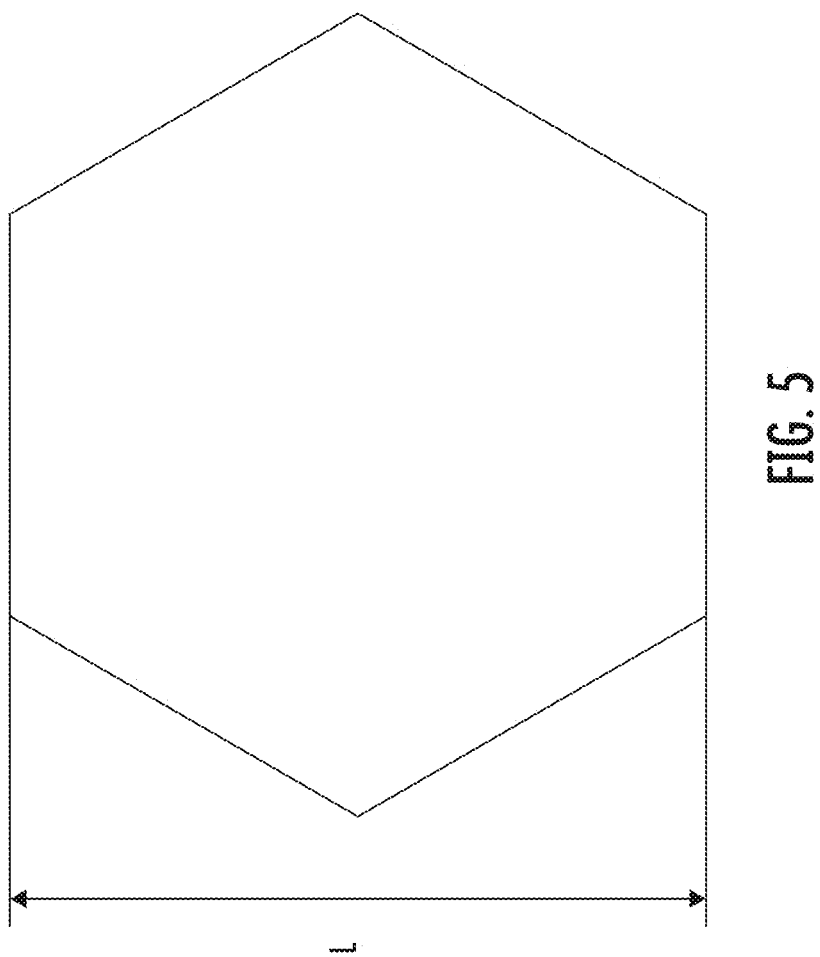
FIG. 5 illustrates an example front view of an example sample optical filter in accordance with examples of the present disclosure.

Referring now to FIG. 5 and FIG. 6, an example front view and an example side view of an example sample optical filter of an example sample filter component are illustrated, respectively.

In the example shown in FIG. 5 and in FIG. 6, the example sample optical filter may be in a shape similar to a hexagonal shape. For example, the sample optical filter may have a side-to-side value L between 10 millimeters and 30 millimeters (for example, 20 millimeters). Additionally, or alternatively, the sample optical filter may have a thickness values T between 0.5 millimeters and 1.5 millimeters (for example, 1 millimeter).

While FIG. 5 and FIG. 6 illustrate an example shape of an example sample optical filter, it is noted that the scope of the present disclosure is not limited to the example shape illustrated in FIG. 5 and FIG. 6. In some examples, an example sample optical filter may be in other shape(s), such as, but not limited to, a triangular shape, a rectangular shape, a circular shape.

While FIG. 5 and FIG. 6 illustrate example measurements of an example sample optical filter, it is noted that the scope of the present disclosure is not limited to these example measurements illustrated in FIG. 5 and FIG. 6. In some examples, an example sample optical filter may have one or more measurements that may be different from the one(s) illustrated in FIG. 5 and FIG. 6.

Figure 7:
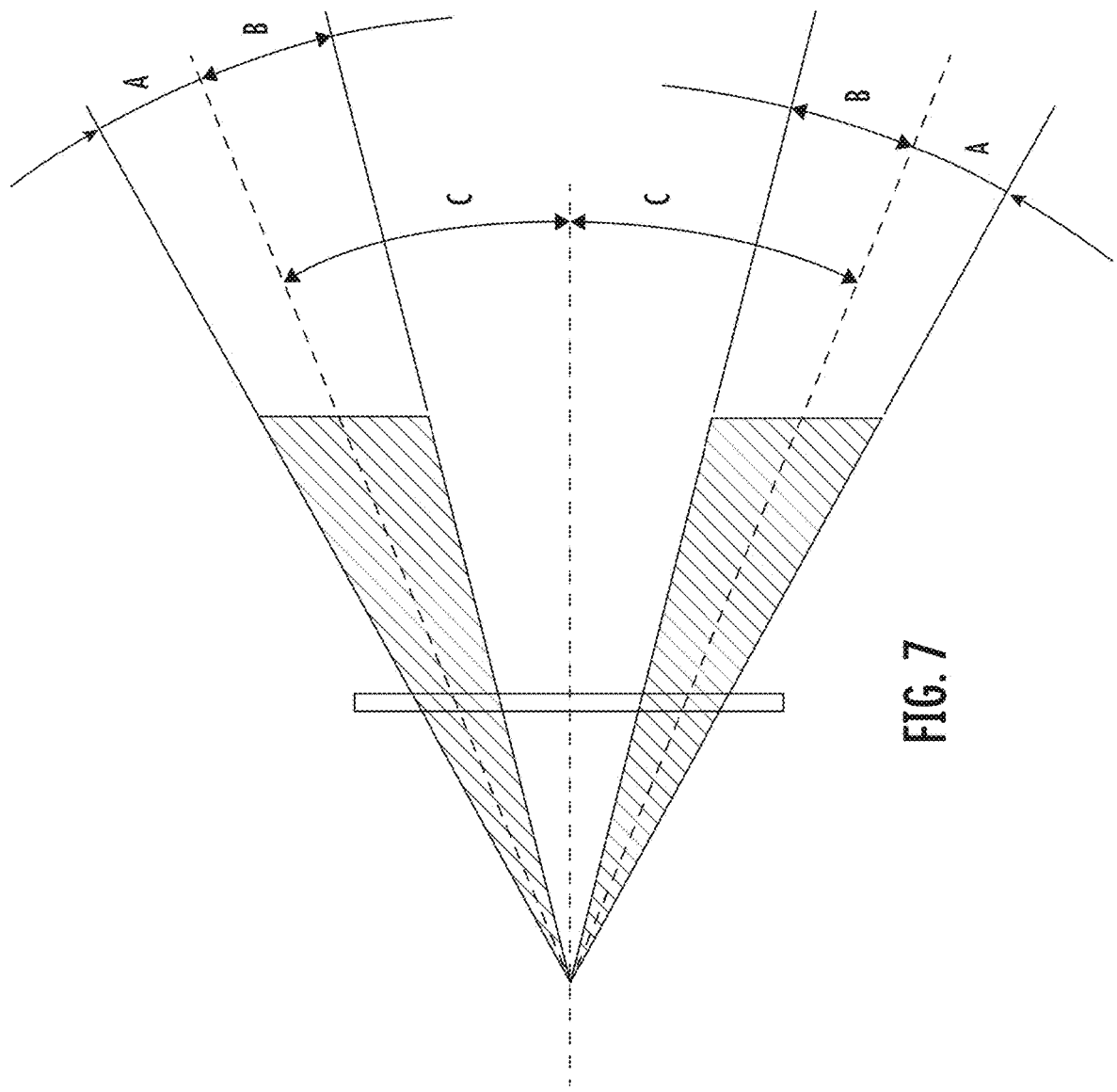
FIG. 7 illustrates an example diagram showing example optical angle(s) associated with an example sample optical filter in accordance with examples of the present disclosure.

Referring now to FIG. 7, an example diagram showing example optical angle(s) associated with an example sample optical filter in accordance with examples of the present disclosure is illustrated.

As described above, an example sample optical filter may receive infrared light from, for example, a mirror component of an example receiver element that may direct infrared light from an infrared light source component to an optical path. The illumination cone of FIG. 7 may illustrate where the infrared light may travel.

In the example shown in FIG. 7, the illumination cone may comprise two cone portions that may mirror each other along the optical axis. In some examples, the angle C between the central axis of each cone portion and the optical axis (also referred to as the "angle of incidence") may be between 16.75 degrees and 20.75 degrees (for example, 18.75 degrees). In some examples, the angle A and the angle B, which may present the angle between the central axis of each cone portion and an outer edge of each cone portion, may be between 4.25 degrees and 8.25 degrees (for example, 6.25 degrees).

While FIG. 7 illustrates example optical angles of an example sample optical filter, it is noted that the scope of the present disclosure is not limited to these example optical angles illustrated in FIG. 7. In some examples, an example sample optical filter may have one or more optical angles that may be different from the one(s) illustrated in FIG. 7.

Figure 8:
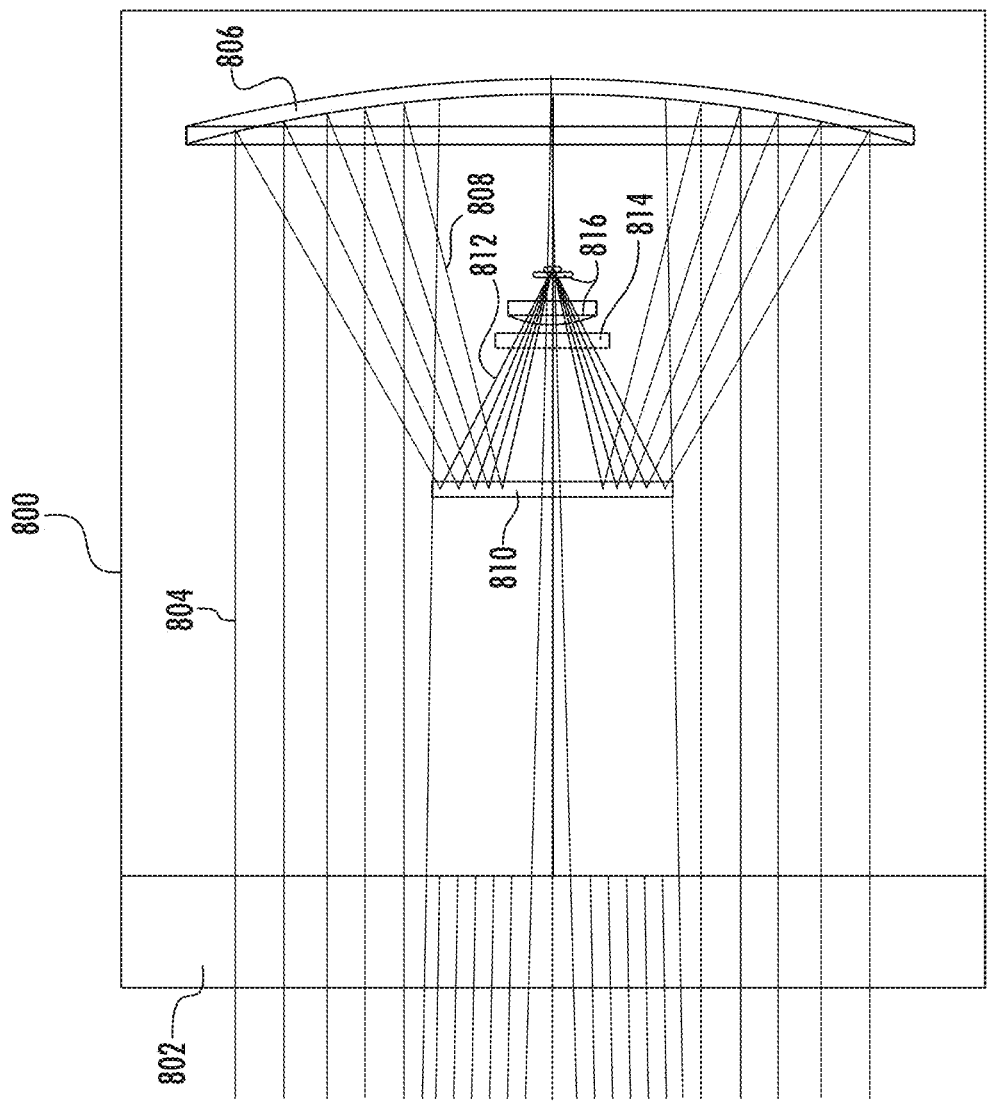
FIG. 8 illustrates an example diagram of at least some example components of an example receiver element in accordance with various examples of the present disclosure.

Referring now to FIG. 8, an example diagram of at least some example components of an example receiver element 800 in accordance with various examples of the present disclosure is illustrated.

Similar to those described above in connection with at least FIG. 2 and FIG. 3, the receiver element 800 may receive and/or detect infrared light. In some examples, the infrared light may be generated by a transmitter element. For example, the transmitter element may comprise an infrared light source component configured to generate infrared light. The infrared light may be emitted from the transmitter element, and may travel along an optical path between the transmitter element and the receiver element 800.

In the example shown in FIG. 8, the infrared light may travel on a first optical path 804 at a first light direction. In such an example, the receiver element 800 may be positioned on the first optical path 804 at the first light direction, such that the infrared light may be received by the receiver element 800.

In some examples, the receiver element 800 may comprise a window lens component 802. In some examples, the infrared light may pass through the window lens component 802. In some examples, the window lens component 802 may comprise a transparent material, such as but not limited to, glass.

In some examples, the receiver element 800 may comprise a mirror component 806. In some examples, the mirror component 806 may comprise a reflective surface that may reflect and/or redirect light. For example, the mirror component 806 may comprise a piece of glass coated with a thin layer of metal, such as but not limited to silver or aluminum.

In some examples, the mirror component 806 may be positioned on the first optical path 804 at the first light direction. In some examples, the mirror component 806 may be configured to direct the infrared light to a second optical path 808 at a second light direction.

In some examples, the receiver element 800 may comprise a sample filter component 810. The sample filter component 810 may comprise a sample optical filter configured to reflect or direct a second portion of the infrared light to a third optical path 812 at a third light direction.

As described above in connection with at least FIG. 2 and FIG. 3, the sample optical filter may be configured to pass a first portion of infrared light within a first wavelength range through the sample optical filter. As such, the second portion of the infrared light that is reflected from the sample optical filter may comprise wavelength(s) that are outside the first wavelength range.

Similar to those described above in connection with at least FIG. 2 and FIG. 3, the sample optical filter may comprise material(s) such as silicon dioxide, sapphire, and/or the like. Additionally, or alternatively, one or more layers of chemical coatings may be applied on one or more surface(s) the sample optical filter, such that the sample optical filter may provide the desired reflective characteristics.

Referring back to FIG. 8, in some examples, the receiver element 800 may comprise a reference filter component 814. The reference filter component 814 may comprise a reference optical filter configured to pass a third portion of the infrared light within one of a second wavelength range or a third wavelength range. For example, the reference optical filter may comprise material(s) such as silicon dioxide, sapphire, and/or the like. Additionally, or alternatively, one or more layers of chemical coatings may be applied on one or more surface(s) the reference optical filter, such that the reference optical filter may provide the desired transmissive and/or reflective characteristics.

In some examples, the receiver element 800 may comprise a reference detector component 816. In some examples, the reference detector component 816 may comprise a reference infrared light detector. For example, a surface of the reference infrared light detector may comprise a photodiode active area that may be configured to detect, measure, and/or identify intensity level of the infrared light. In some examples, the photodiode active area may comprise indium gallium arsenide (InGaAs). Additionally, or alternatively, the reference detector component 816 may comprise other suitable infrared detecting device.

In some examples, the reference filter component 814 and the reference detector component 816 may be positioned on the third optical path 812 and/or at the third light direction. For example, as shown in FIG. 8, infrared light (reflected from the sample filter component 810) may travel on the third optical path 812 at the third light direction through the reference optical filter of the reference filter component 814, and may be received by the reference infrared light detector of the reference detector component 816.

In the example shown in FIG. 8, the reference detector component 816 may be positioned at a coaxial arrangement relative to or positioned coaxially with the reference filter component 814. For example, the reference infrared light detector of the reference detector component 816 may be positioned at a coaxial arrangement relative to or positioned coaxially with the reference optical filter of the reference filter component 814, such that an optical axis may pass through the center of the reference infrared light detector and the center of the reference optical filter. In some examples, a surface of the reference optical filter may be in a perpendicular arrangement with the optical axis. In some examples, a surface of the reference infrared light detector (for example, a surface that comprises a photodiode active area) may be in a perpendicular arrangement with the optical axis.

In some examples, the sample filter component 810, the reference detector component 816, and the reference filter component 814 may be positioned at a coaxial arrangement relative to or positioned coaxially with each other, such that the optical axis may pass through the center of the sample filter component 810, the reference detector component 816, and the center of the reference filter component 814.

In some examples, the mirror component 806, the sample filter component 810, the reference detector component 816, and the reference filter component 814 may be disposed within the receiver element 800. For example, each of the mirror component 806, the sample filter component 810, the reference detector component 816, and the reference filter component 814 may be securely positioned with respect an inner surface of the receiver element 800 through one or more supporting beams and/or other supporting structure.

As described, the reference filter component 814 is configured to pass a third portion of the infrared light within one of a second wavelength range or a third wavelength range. Accordingly, the reference detector component 816 may be configured to generate a second light intensity indication corresponding to the third portion of the infrared light within one of the second wavelength range or the third wavelength range that has passed through the reference filter component 814.

Figure 9:
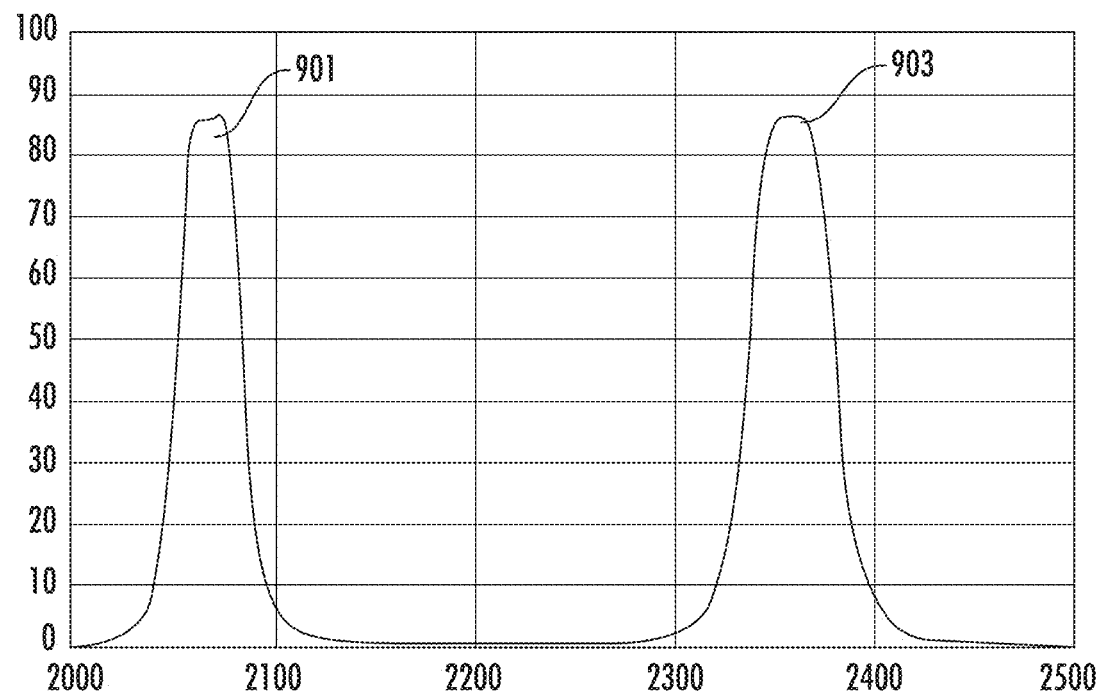
FIG. 9 illustrates an example diagram showing example wavelength range(s) associated with an example reference filter component in accordance with examples of the present disclosure.
Figure 10:
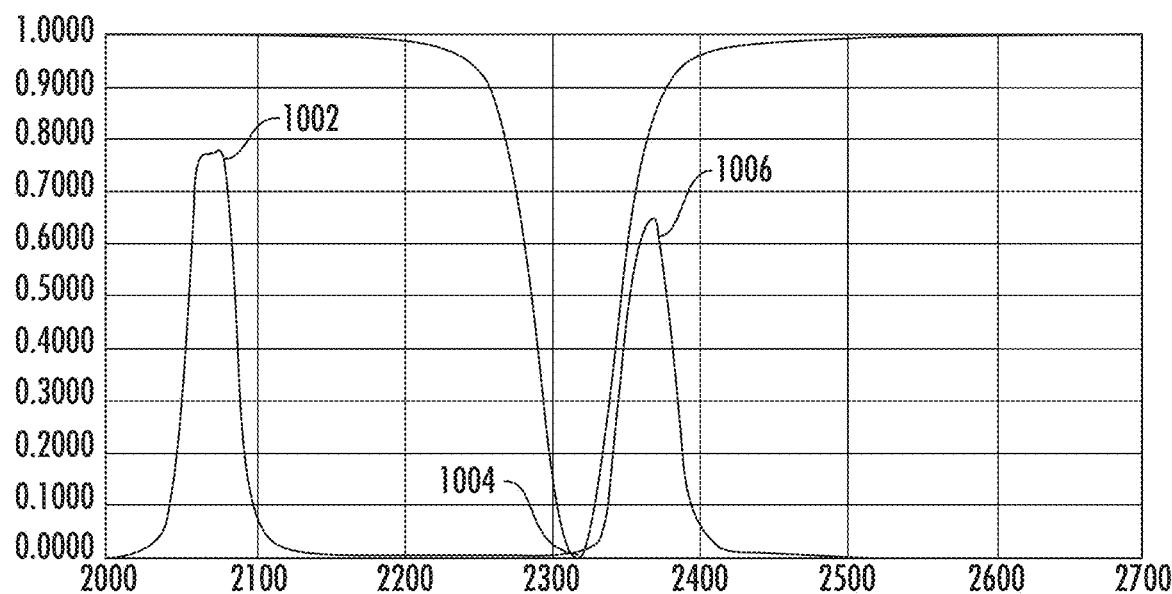
FIG. 10 illustrates an example diagram showing example wavelength range(s) associated with an example sample filter component and an example reference filter component in accordance with examples of the present disclosure.

Referring now to FIG. 9 and FIG. 10, example diagrams showing example wavelength ranges associated with an example reference filter component are illustrated. For example, the example diagrams may illustrate example intensity levels associated with different wavelengths as detected by example reference detector components based on infrared light that has passed through an example reference filter component.

In particular, FIG. 9 illustrates example wavelength ranges of infrared light that passes through an example reference filter component, and the infrared light is not reflected from an example sample filter component prior to passing through the example reference filter component. In other words, FIG. 9 illustrates example transmission characteristics of an example reference filter component without any effects on the wavelength ranges caused by the example sample filter component.

As described, the reference filter component may comprise a reference optical filter configured to pass a third portion of the infrared light within one of a second wavelength range or a third wavelength range. In the example shown in FIG. 9, the second wavelength range may be centered around a first peak 901. The center wavelength corresponding to the first peak 901 may be between 2000 nanometers and 2100 nanometers (for example, 2065 nanometers). In some examples, the wavelength range associated with the center wavelength may have a FWHM value between 25 nanometers and 45 nanometers (for example, 35 nanometers). In some examples, the peak transmission range of the example reference filter component may be between 60% and 80% (for example, 70%).

In the example shown in FIG. 9, the third wavelength range may be centered around a second peak 903. In some examples, the center wavelength corresponding to the second peak 903 may be between 2300 nanometers and 2400 nanometers (for example, 2360 nanometers). In some examples, the wavelength range associated with the center wavelength may have a FWHM value between 30 nanometers and 60 nanometers (for example, 47 nanometers). In some examples, the peak transmission range of the example reference filter component may be between 60% and 80% (for example, 70%).

As described above, the reference filter component may filter the infrared light at wavelength(s) and/or wavelength(s) ranges where the target gaseous substance may not or may be less likely to absorb the infrared light. As such, the center wavelength and the FWHM value of the first peak 901 and/or the second peak 903 may be determined such that the second wavelength range or the third wavelength range may not or may be less likely to overlap with the absorption spectra associated with hydrocarbon gaseous substance(s).

While the above description provides some example values associated with the wavelength range and the reference filter component, it is noted that that the scope of the present disclosure is not limited to these example values and example methods. In some examples, the wavelength range and/or the reference filter component may be associated with other values.

In the example shown in FIG. 9, the first peak 901 and the second peak 903 may be symmetrical or approximately symmetrical. However, to meet requirements for desired performance, it may be necessary for a reference filter component to create two peaks that are asymmetrical. In some examples, the first peak may have a relatively high intensity level (e.g. a higher transmission rate of the infrared light and/or a larger bandwidth of wavelengths). In some examples, the second peak may have a relatively low or reduced intensity level (e.g. a lower transmission rate of the infrared light and/or a smaller bandwidth of wavelengths) as compared to that of the first peak. It may be difficult to design and manufacture a reference filter component that may produce asymmetric double peaks. For example, many layers of coating and long run times may be required to produce such a reference filter component, which may lead to instability, variation in performance, and low yields.

Various examples of the present disclosure may overcome these technical challenges. In the examples shown in FIG. 2, FIG. 3, and FIG. 8, examples of the present disclosure may provide a receiver element with a sample filter component and a reference filter component. In some examples, the sample filter component may be positioned at a first coaxial arrangement relative to or positioned coaxially with the reference filter component. Through such an arrangement, the sample filter component may transmit or pass a portion of the infrared light, and may reflect or redirect another portion of the infrared light to the reference filter component. Due to the transmission of infrared light, the sample filter component may remove some energy from the infrared light before the infrared light arrives at the reference filter component. As such, infrared light that passes through the reference filter component may have a lower intensity level at the second peak as compared to the intensity level of the first peak.

Referring now to FIG. 10, example wavelength ranges of infrared light that passes through an example reference filter component are illustrated. In particular, the infrared light is reflected from an example sample filter component prior to passing through the example reference filter components. In other words, FIG. 10 illustrates example transmission characteristics of an example reference filter component with effects on the wavelength ranges caused by the example sample filter component. Example arrangements between the sample filter component and the reference filter component are illustrated and described above in connection with at least FIG. 2, FIG. 3, and FIG. 8.

As described above, the sample filter component may be configured to pass or transmit a portion of infrared light within a first wavelength range, and may be configured to reflect a portion of infrared light outside a first wavelength range of infrared light. In the example shown in FIG. 10, the curve 1004 may be associated with wavelength range(s) of infrared light that is reflected from an example sample filter component to an example reference filter component.

As described above, the reference filter component may be configured to pass or transmit a portion of the infrared light (reflected from the sample filter component) within one of a second wavelength range or a third wavelength range. In the example shown in FIG. 10, the second wavelength range may be centered around a first peak 1002, and the third wavelength range may be centered around a second peak 1006.

In some examples, the first wavelength range may be between the second wavelength range and the third wavelength range. For example, the first wavelength range centered around the valley of the curve 1004 may be between the second wavelength range centered around the first peak 1002 and the third wavelength range centered around the second peak 1006.

In some examples, the first wavelength range may at least partially overlap with the third wavelength range. For example, the first wavelength range centered around the valley of the curve 1004 may at least partially overlap with the third wavelength range centered around the second peak 1006. Because of the transmission characteristics of the sample filter component (as shown in curve 1004), energy of infrared light near the second peak 1006 may be reduced, therefore examples of the present disclosure may provide a reference filter component that may create two peaks that are asymmetrical as shown in FIG. 10.

Figure 12:
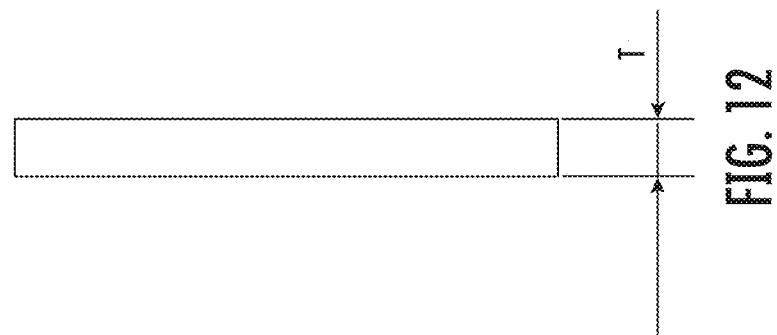
FIG. 12 illustrates an example side view of an example reference optical filter in accordance with examples of the present disclosure.
Figure 11:
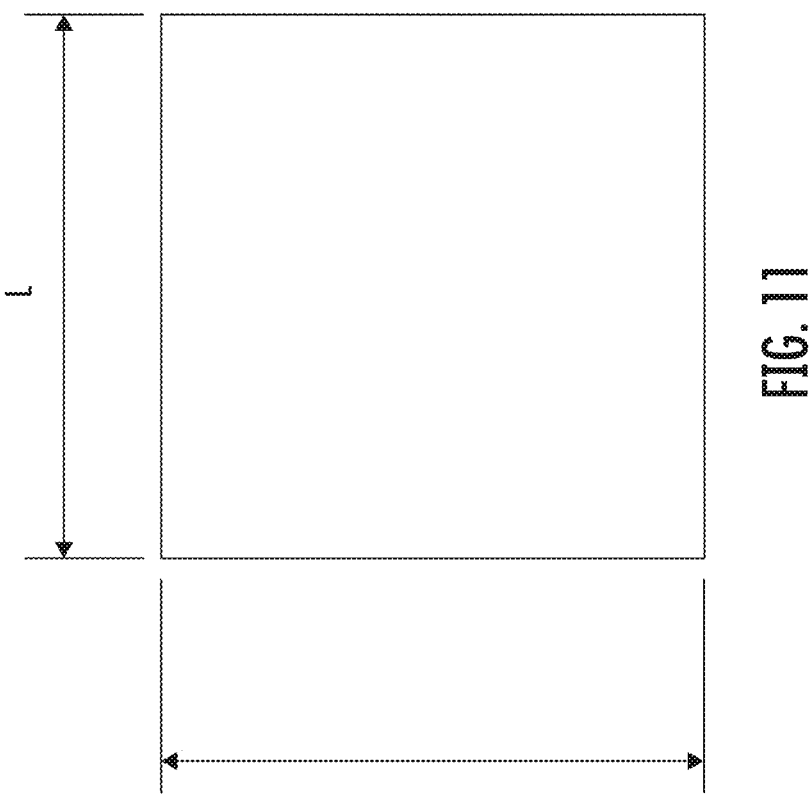
FIG. 11 illustrates an example front view of an example reference optical filter in accordance with examples of the present disclosure.

Referring now to FIG. 11 and FIG. 12, an example front view and an example side view of an example reference optical filter of an example reference filter component are illustrated, respectively.

In the example shown in FIG. 11 and in FIG. 12, the example reference optical filter may be in a shape similar to a quadrilateral shape (for example, a rectangular shape or a square shape). In some examples, the reference optical filter may have a length value L between 6 millimeters and 12 millimeters (for example, 9 millimeters). Additionally, or alternatively, the reference optical filter may have a thickness values T between 0.5 millimeters and 1.5 millimeters (for example, 1 millimeter).

While FIG. 11 and FIG. 12 illustrate an example shape of an example reference optical filter, it is noted that the scope of the present disclosure is not limited to the example shape illustrated in FIG. 11 and FIG. 12. In some examples, an example reference optical filter may be in other shape(s), such as, but not limited to, a triangular shape, a hexagonal shape, a circular shape.

While FIG. 11 and FIG. 12 illustrate example measurements of an example reference optical filter, it is noted that the scope of the present disclosure is not limited to these example measurements illustrated in FIG. 11 and FIG. 12. In some examples, an example reference optical filter may have one or more measurements that may be different from the one(s) illustrated in FIG. 11 and FIG. 12.

Figure 13:
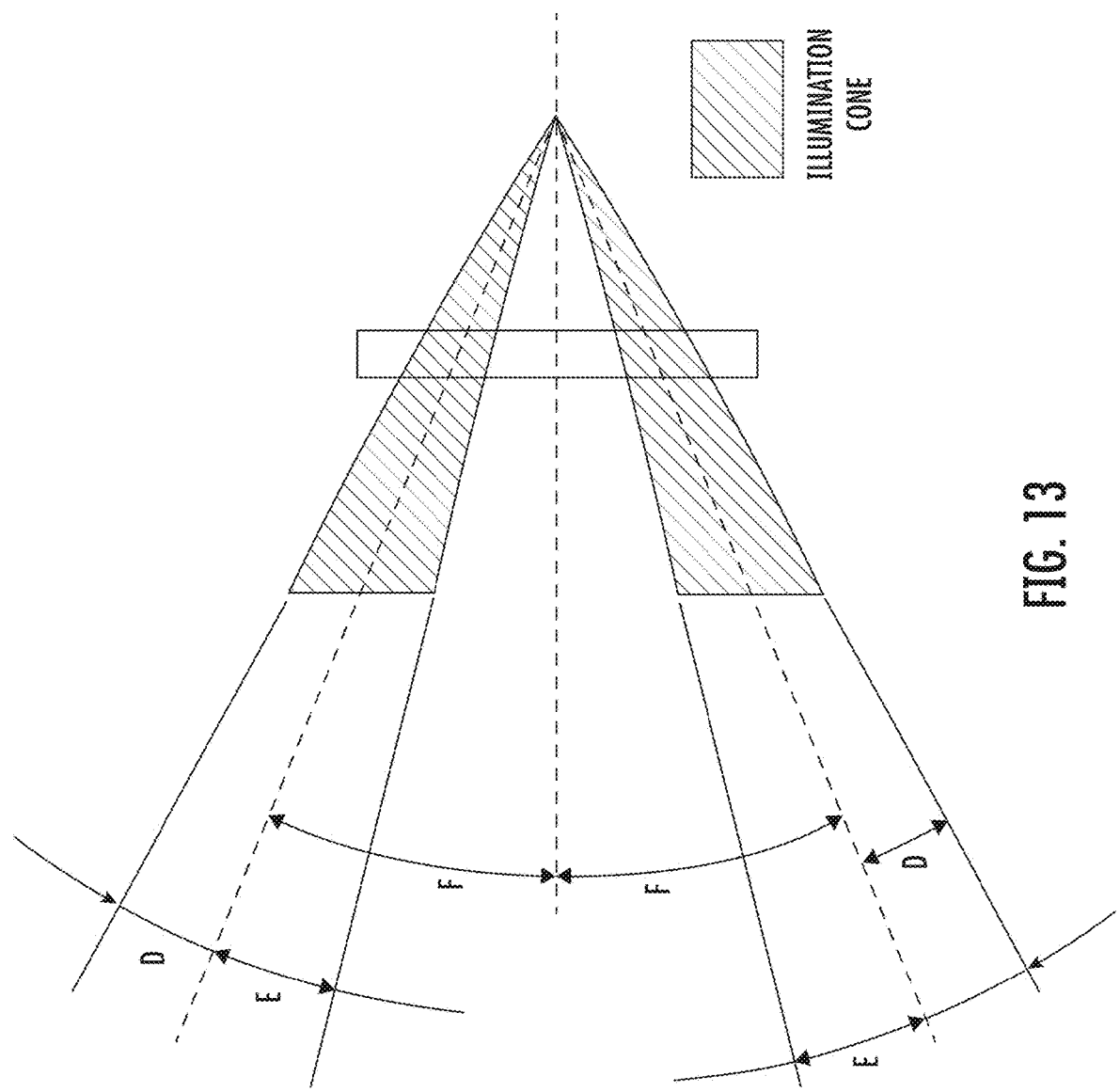
FIG. 13 illustrates an example diagram showing example optical angle(s) associated with an example reference optical filter in accordance with examples of the present disclosure.

Referring now to FIG. 13, an example diagram showing example optical angle(s) associated with an example reference optical filter in accordance with examples of the present disclosure is illustrated.

As described above, an example reference optical filter may receive infrared light from, for example, a sample optical filter of a sample filter component that may reflect infrared light from a mirror component to an optical path. The illumination cone of FIG. 13 may illustrate where the infrared light may travel.

In the example shown in FIG. 13, the illumination cone may comprise two cone portions that may mirror each other along the optical axis. In some examples, the angle F between the central axis of each cone portion and the optical axis (also referred to as the "angle of incidence") may be between 16.75 degrees and 20.75 degrees (for example, 18.75 degrees). In some examples, the angle D and the angle E, which may present the angle between the central axis of each cone portion and an outer edge of each cone portion, may be between 4.25 degrees and 8.25 degrees (for example, 6.25 degrees).

While FIG. 13 illustrates example optical angles of an example reference optical filter, it is noted that the scope of the present disclosure is not limited to these example optical angles illustrated in FIG. 13. In some examples, an example reference optical filter may have one or more optical angles that may be different from the one(s) illustrated in FIG. 13.

Referring now to FIG. 14, FIG. 15, FIG. 16, and FIG. 17, example diagrams showing example wavelength ranges associated with example receiver elements are illustrated.

Figure 14:
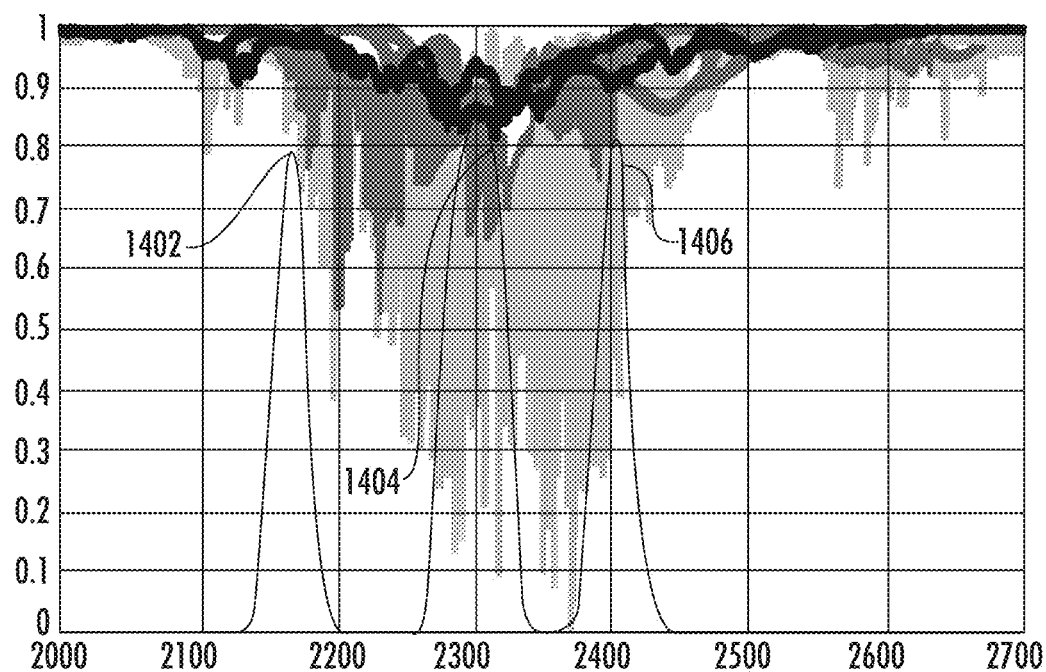
FIG. 14 illustrates an example diagram showing example wavelength range(s) associated with an example receiver element in accordance with examples of the present disclosure.

In particular, FIG. 14 illustrates a comparison between absorption wavelength range(s) associated with hydrocarbon gaseous substances and example wavelengths of an receiver element. The receiver element may comprise a sample filter component and a reference filter component. For the example shown in FIG. 14, the sample filter component may not be positioned at a coaxial arrangement relative to or positioned coaxially with the reference filter component, and may not reflect infrared light to the reference filter component.

As describe above, the sample filter component may comprise a sample optical filter configured to pass a first portion of infrared light within a first wavelength range that may center around the peak 1404. The reference filter component may comprise a reference optical filter configured to pass a second portion of infrared light within a second wavelength range that may center around the peak 1402 or a third wavelength range that may center around the peak 1406. In the example shown in FIG. 14, the peak 1406 may overlap with at least some of the absorption wavelength range(s) associated with hydrocarbon gaseous substances. As such, readings of hydrocarbon gaseous substances may not be normalized.

Figure 15:
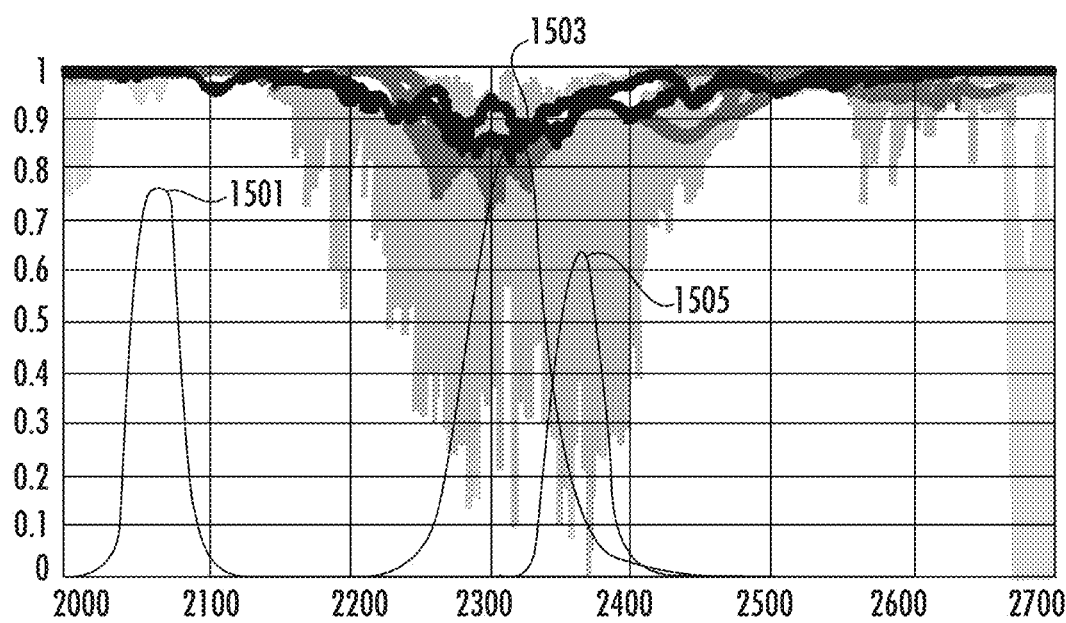
FIG. 15 illustrates an example diagram showing example wavelength range(s) associated with an example receiver element in accordance with examples of the present disclosure.

In contrast with FIG. 14, FIG. 15 illustrates a comparison between absorption wavelength range(s) associated with hydrocarbon gaseous substances and example wavelengths of an receiver element that implements examples of the present disclosure. For the example shown in FIG. 15, the sample filter component may be positioned at a coaxial arrangement relative to or positioned coaxially with the reference filter component, and may reflect infrared light to the reference filter component.

As describe above, the sample filter component of the receiver element may comprise a sample optical filter configured to pass a first portion of infrared light within a first wavelength range that may center around the peak 1503. The reference filter component of the receiver element may comprise a reference optical filter configured to pass a second portion of infrared light within a second wavelength range that may center around the peak 1501 or a third wavelength range that may center around the peak 1505. Comparing FIG. 15 with FIG. 14, the peak 1505 of FIG. 15 is smaller than the peak 1406 of FIG. 14. As such, the overlap between the third wavelength range with the absorption wavelength range(s) associated with hydrocarbon gaseous substances may be reduced, and readings of hydrocarbon gaseous substances may be more normalized.

Figure 16:
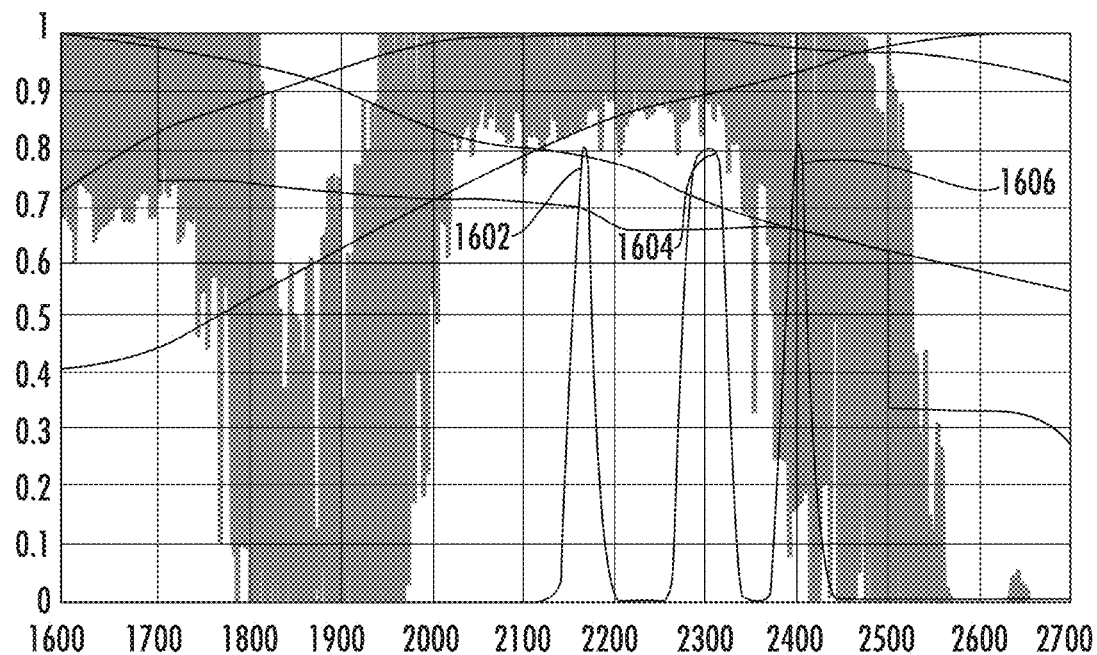
FIG. 16 illustrates an example diagram showing example wavelength range(s) associated with an example receiver element in accordance with examples of the present disclosure.
Figure 17:
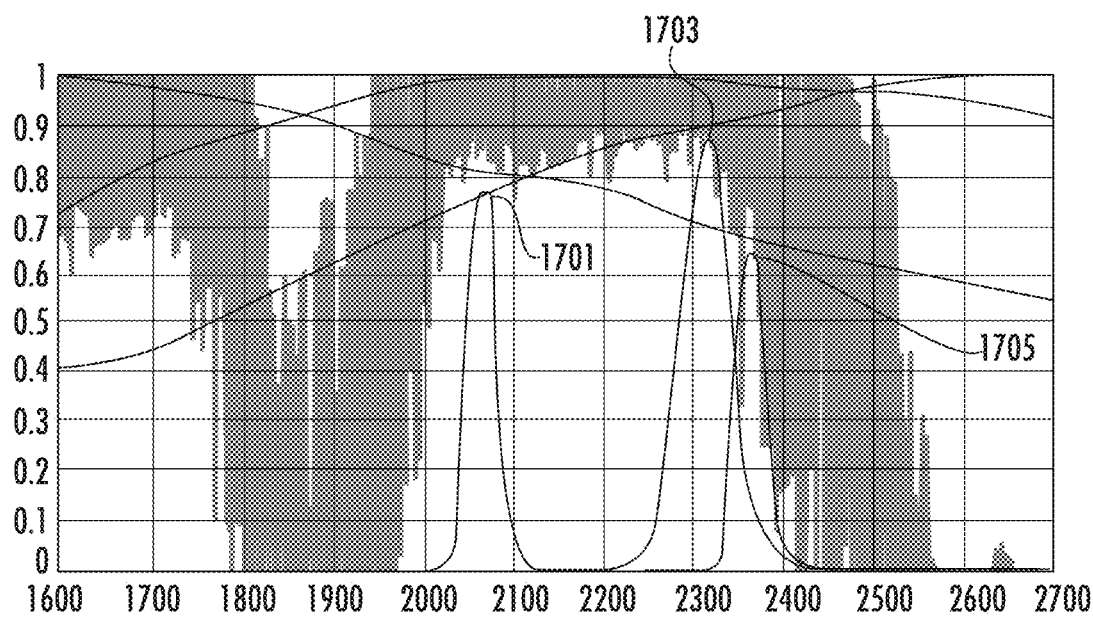
FIG. 17 illustrates an example diagram showing example wavelength range(s) associated with an example receiver element in accordance with examples of the present disclosure.

FIG. 16 illustrates a comparison between absorption wavelength range(s) associated with water, fog (and other non-target substances) and example wavelengths of an receiver element. The receiver element may comprise a sample filter component and a reference filter component. For the example shown in FIG. 16, the sample filter component may not be positioned at a coaxial arrangement relative to or positioned coaxially with the reference filter component, and may not reflect infrared light to the reference filter component.

As described above, the sample filter component may comprise a sample optical filter configured to pass a first portion of infrared light within a first wavelength range that may center around the peak 1604. The reference filter component may comprise a reference optical filter configured to pass a second portion of infrared light within a second wavelength range that may center around the peak 1602 or a third wavelength range that may center around the peak 1606. In the example shown in FIG. 16, the peak 1606 may overlap with at least some of the absorption wavelength range(s) associated with non-target substances. As such, the receiver element may provide a higher than desirable sensitivity to non-target substances.

In contrast with FIG. 15, FIG. 16 illustrates a comparison between absorption wavelength range(s) associated with water, fog (and other non-target substances) and example wavelengths of an receiver element that implements examples of the present disclosure. For the example shown in FIG. 17, the sample filter component may be positioned at a coaxial arrangement relative to or positioned coaxially with the reference filter component, and may reflect infrared light to the reference filter component.

As describe above, the sample filter component of the receiver element may comprise a sample optical filter configured to pass a first portion of infrared light within a first wavelength range that may center around the peak 1703. The reference filter component of the receiver element may comprise a reference optical filter configured to pass a second portion of infrared light within a second wavelength range that may center around the peak 1701 or a third wavelength range that may center around the peak 1705. Comparing FIG. 17 with FIG. 16, the peak 1705 of FIG. 17 does not overlap or has very little overlap with absorption wavelength range(s) associated with water, fog (and other non-target substances). As such, the sensitivity of the receiver element to non-target substances may be reduced.

It is to be understood that the disclosure is not to be limited to the specific examples disclosed, and that modifications and other examples are intended to be included within the scope of the appended claims. Although specific terms are employed herein, they are used in a generic and descriptive sense only and not for purposes of limitation, unless described otherwise.

The invention claimed is:

1. A gas detecting device comprising a receiver element, wherein the receiver element comprises a sample filter component and a reference filter component, wherein the sample filter component is positioned coaxially with the reference filter component and comprises a sample optical filter configured to pass a first portion of infrared light within a first wavelength range, based at least in part on an absorption wavelength range associated with a target gaseous substance, and configured to reflect a second portion of the infrared light to the reference filter component, wherein the reference filter component comprises a reference optical filter configured to pass the second portion of the infrared light within at least a second wavelength range in which the target gaseous substance does not absorb infrared light.

2. The gas detecting device of claim 1, wherein the first wavelength range at least partially overlaps with the second wavelength range.

3. The gas detecting device of claim 1, wherein the first wavelength range is between the second wavelength range and a third wavelength range.

4. The gas detecting device of claim 1, wherein the receiver element further comprises:
   a sample detector component comprising a sample infrared light detector configured to generate a first light intensity indication corresponding to the first portion of the infrared light within the first wavelength range; and
   a reference detector component comprising a reference infrared light detector configured to generate a second light intensity indication corresponding to the second portion of the infrared light within at least one of the second wavelength range or a third wavelength range.

5. The gas detecting device of claim 4, wherein the sample infrared light detector of the sample detector component is positioned coaxially with the sample optical filter of the sample filter component.

6. The gas detecting device of claim 4, wherein the reference infrared light detector of the reference detector component is positioned coaxially with the reference optical filter of the reference filter component.

7. The gas detecting device of claim 4, wherein the sample optical filter of the sample filter component is positioned between the sample infrared light detector of the sample detector component and the reference infrared light detector of the reference detector component.

8. The gas detecting device of claim 4, wherein the reference optical filter of the reference filter component is positioned between the sample optical filter of the sample filter component and the reference infrared light detector of the reference detector component.

9. The gas detecting device of claim 4, wherein the sample optical filter of the sample filter component, the sample infrared light detector of the sample detector component, the reference optical filter of the reference filter component, and the reference infrared light detector of the reference detector component are positioned coaxially with each other.

10. The gas detecting device of claim 1, wherein the gas detecting device further comprises a transmitter element, wherein the transmitter element comprises an infrared light source component configured to generate infrared light on a first optical path at a first light direction, wherein the receiver element is positioned on the first optical path at the first light direction.

11. The gas detecting device of claim 10, wherein the receiver element comprises a mirror component positioned on the first optical path at the first light direction and configured to direct the infrared light to a second optical path at a second light direction.

12. The gas detecting device of claim 11, wherein the receiver element comprises a sample detector component, wherein the sample filter component and the sample detector component are positioned on the second optical path at the second light direction.

13. The gas detecting device of claim 12, wherein the sample detector component is positioned coaxially with the sample filter component.

14. The gas detecting device of claim 12, wherein the sample detector component is configured to generate a first light intensity indication corresponding to the first portion of the infrared light within the first wavelength range.

15. The gas detecting device of claim 14, wherein the sample filter component is configured to direct the second portion of the infrared light outside the first wavelength range to a third optical path at a third light direction.

16. The gas detecting device of claim 15, wherein the receiver element comprises a reference detector component, wherein the reference filter component and the reference detector component are positioned on the third optical path at the third light direction.

17. The gas detecting device of claim 16, wherein the reference detector component is positioned coaxially with the reference filter component.

18. The gas detecting device of claim 16, wherein the reference filter component is configured to pass a third portion of the infrared light within one of the second wavelength range or a third wavelength range, wherein the reference detector component is configured to generate a second light intensity indication corresponding to the third portion of the infrared light within one of the second wavelength range or the third wavelength range.

* * * * *